(12) United States Patent
Harris et al.

(10) Patent No.: US 10,799,121 B2
(45) Date of Patent: Oct. 13, 2020

(54) METHOD FOR QUANTIFYING PLAQUE IN PET ANIMALS

(71) Applicant: Mars, Incorporated, McLean, VA (US)

(72) Inventors: Stephen James Harris, Leicestershire (GB); Corryn Victoria Wallis, Leicestershire (GB); Judith Margaret Allsopp, Leicestershire (GB); Alison Colyer, Leicestershire (GB)

(73) Assignee: MARS, Incorporated, McLean, VA (US)

(*) Notice: Subject to any disclaimer, the term of this patent is extended or adjusted under 35 U.S.C. 154(b) by 0 days.

(21) Appl. No.: 16/700,675

(22) Filed: Dec. 2, 2019

(65) Prior Publication Data

US 2020/0121191 A1   Apr. 23, 2020

Related U.S. Application Data

(63) Continuation of application No. 15/525,538, filed as application No. PCT/GB2015/053464 on Nov. 13, 2015, now Pat. No. 10,492,692.

(30) Foreign Application Priority Data

Nov. 14, 2014  (GB) .................................. 1420273.3

(51) Int. Cl.
*G06K 9/00* (2006.01)
*A61B 10/00* (2006.01)
(Continued)

(52) U.S. Cl.
CPC .............. *A61B 5/0088* (2013.01); *A61B 1/24* (2013.01); *A61B 5/0071* (2013.01); *A61D 5/00* (2013.01);
(Continued)

(58) Field of Classification Search
USPC ....... 382/100, 103, 108, 128, 162, 168, 173, 382/181, 190, 199, 209, 219, 232, 254,
(Continued)

(56) References Cited

U.S. PATENT DOCUMENTS 5,382,163 A   1/1995  Putnam
6,024,562 A   2/2000  Hibst et al.
(Continued)

FOREIGN PATENT DOCUMENTS

EP   0113152      7/1984
JP   2006174977 A 7/2006

OTHER PUBLICATIONS

"A Statistical Modeling Approach to Computer-Aided Mar. 6, 2014 Quantification of Dental Biofilnn" Awais Mansoor, Member, IEEE, Valery Patsekin, Dale Scherl, J. Paul Robinson, Member, IEEE, and Bartlomiej Rajwa Mar. 6, 2014.*
(Continued)

*Primary Examiner* — Seyed H Azarian
(74) *Attorney, Agent, or Firm* — MARS, Incorporated KSJLaw, LLC

(57) ABSTRACT

The present invention relates to methods for detecting and quantifying the plaque levels and/or lesions in companion animals, and the use of such information during trials of oral health products. The methods disclosed enable the trialling of companion animals for a shorter period of time, without the need for long and expensive trials on oral health products to be conducted. The methods described are conducted on conscious pet animals.

7 Claims, 25 Drawing Sheets

(51) Int. Cl.
  *A61B 5/00* (2006.01)
  *A61B 1/24* (2006.01)
  *A61D 5/00* (2006.01)
(52) U.S. Cl.
  CPC ....... *A61B 2503/40* (2013.01); *A61B 2576/02* (2013.01)
(58) Field of Classification Search
  USPC ................ 382/276, 285–291, 305, 312, 321; 424/401, 9.6, 134.1; 378/46; 433/215
  See application file for complete search history.

(56) References Cited

U.S. PATENT DOCUMENTS

| | | | |
|---|---|---|---|
| 6,102,704 | A | 8/2000 | Eibofner et al. |
| 6,404,984 | B1 | 6/2002 | Parvulescu et al. |
| 8,041,005 | B2 | 10/2011 | Boyden et al. |
| 8,647,119 | B1* | 2/2014 | Nagai ................. A61B 5/0088 433/215 |
| 9,042,967 | B2 | 5/2015 | Dacosta et al. |
| 2004/0254478 | A1 | 12/2004 | De Josselin De Jong et al. |
| 2009/0086905 | A1* | 4/2009 | Boyden ................ G01N 23/223 378/46 |
| 2010/0183523 | A1 | 7/2010 | Wagner |
| 2010/0322987 | A1 | 12/2010 | Robinson et al. |
| 2011/0117025 | A1* | 5/2011 | Dacosta .................. A61B 5/01 424/9.6 |
| 2013/0323673 | A1 | 12/2013 | Hakomori et al. |
| 2014/0093457 | A1* | 4/2014 | Nagai .................... A61K 45/06 424/9.6 |
| 2014/0302027 | A1* | 10/2014 | Hajishengallis ........ A61P 29/00 424/134.1 |
| 2014/0314819 | A1* | 10/2014 | Scherl ..................... A61K 6/69 424/401 |
| 2019/0142275 | A1 | 5/2019 | Harris et al. |

OTHER PUBLICATIONS

"Nutrient Profiles for Dog Foods", Association of American Feed Control Officials Incorporated, pp. 110-119, 1994.
"Nutrient Requirements for Dogs", National Academy Press, Mar. 1, 1985, pp. 2-5, 7-9, 12-14, 44-45.
Hennet, et al., "Evaluation of the Logan & Boyce Plaque Index for the Study of Dental Plaque Accumulation in Dogs", Res. Vet. Sci., Apr. 2006, 80(2)175-180.
Logan, et al., "Oral Health Assessment in Dogs: Parameters and Methods", J. Vet. Dent., Aug. 1994, 11(2):58-63 Abstract Only (1 pg.).
Mansoor, et al., "A Statistical Modeling Approach to Computer-Aided Quantification of Dental Biofilm", IEEE Journal of Biomedical and Health Informatics, vol. 19, No. 1, pp. 358-367, Jan. 2015.
Scherl, et al., "Application of the Gingival Contour Plaque Index: Six-Month Plaque and Gingivitis Study", J. Vet. Dent., 2009, 26(1):23-27.

* cited by examiner

| Data | # Teeth | Variance Components | | | Adult diet % plaque coverage | Difference in Means (95% CI) | % Reduction from Adult (95% CI) | Diet p-value |
| --- | --- | --- | --- | --- | --- | --- | --- | --- |
| | | Between Cat | Between Tooth Between Cat | Within | | | | |
| All (Upper and Lower) | 14 | 51.5 | 406.1 | 220.7 | 53.9 | 7.74 (5.45, 10.03) | 14.36 (10.11, 18.6) | 0.0000 |
| 104, 204 | 2 | 90.8 | 22.2 | 106.4 | 29.3 | -4.52 (-8.72, -0.32) | -15.46 (-29.82, -1.1) | 0.0348 |
| 107, 207 | 2 | 31.8 | 35.9 | 275.0 | 59.7 | 12.07 (5.35, 18.8) | 20.23 (8.96, 31.49) | 0.0004 |
| 108, 208 | 2 | 64.8 | 5.2 | 60.9 | 85.9 | 8.97 (5.8, 12.15) | 10.44 (6.74, 14.14) | 0.0000 |
| 104, 204 107, 207 | 4 | 23.1 | 171.7 | 224.1 | 44.5 | 3.84 (-0.47, 8.14) | 8.62 (-1.05, 18.28) | 0.0806 |
| 107, 207 108, 208 | 4 | 0.0 | 260.4 | 167.7 | 72.9 | 10.65 (6.92, 14.38) | 14.6 (9.49, 19.71) | 0.0000 |
| 104, 204 107, 207 108, 208 | 6 | 0.0 | 485.8 | 171.5 | 58.4 | 5.66 (2.58, 8.74) | 9.69 (4.41, 14.96) | 0.0003 |

FIG. 21

| Numbering of teeth in whole mouth and VOHC recommended teeth in dogs in square brackets | | | |
|---|---|---|---|
| Upper | | Lower | |
| Right | Left | Right | Left |
| I1 (101) | I1 (201) | I1 (301) | I1 (401) |
| I2 (102) | I2 (202) | I2 (302) | I2 (402) |
| [I3 (103)] | [I3 (203)] | I3 (303) | I3 (403) |
| [C (104)] | [C (204)] | [C (304)] | [C (404)] |
| P1 (105) | P1 (205) | P1 (305) | P1 (405) |
| P2 (106) | P2 (206) | P2 (306) | P2 (406) |
| [P3 (107)] | [P3 (207)] | [P3 (307)] | [P3 (407)] |
| [P4 (108)] | [P4 (208)] | [P4 (308)] | [P4 (408)] |
| [M1 (109)] | [M1 (209)] | [M1 (309)] | [M1 (409)] |
| M2 (110) | M2 (210) | M2 (310) | M2 (410) |

FIG. 22A

| Recommended VOHC teeth (dog) total of 18 teeth | | | |
|---|---|---|---|
| Upper | | Lower | |
| Right | Left | Right | Left |
| I3 (103) | I3 (203) | | |
| C (104) | C (204) | C (304) | C (404) |
| P3 (107) | P3 (207) | P3 (307) | P3 (407) |
| P4 (108) | P4 (208) | P4 (308) | P4 (408) |
| M1 (109) | M1 (209) | M1 (309) | M1 (409) |
| Recommended VOHC teeth (cat) total of 18 teeth | | | |
| Upper | | Lower | |
| Right | Left | Right | Left |
| C (104) | C (204) | C (304) | C (404) |
| P3 (107) | P3 (207) | P3 (307) | P3 (407) |
| P4 (108) | P4 (208) | P4 (308) | P4 (408) |
| | | M1 (309) | M1 (409) |

FIG. 22B

| Teeth assessed in Figures 4/14(*) | | | |
|---|---|---|---|
| Upper | | Lower | |
| Right | Left | Right | Left |
| *I1 (101) | *I1 (201) | I1 (301) | I1 (401) |
| *I2 (102) | *I2 (202) | I2 (302) | I2 (402) |
| *I3 (103) | *I3 (203) | I3 (303) | I3 (403) |
| *C (104) | *C (204) | C (304) | C (404) |
| *P1 (105) | *P1 (205) | P1 (305) | P1 (405) |
| *P2 (106) | *P2 (206) | P2 (306) | P2 (406) |
| *P3 (107) | *P3 (207) | P3 (307) | P3 (407) |
| *P4 (108) | *P4 (208) | P4 (308) | P4 (408) |
| M1 (109) | M1 (209) | M1 (309) | M1 (409) |
| M2 (110) | M2 (210) | M2 (310) | M2 (410) |

FIG. 23A

| Teeth assessed in Figures 5/6/9 (*) | | | |
|---|---|---|---|
| Upper | | Lower | |
| Right | Left | Right | Left |
| I1 (101) | I1 (201) | I1 (301) | I1 (401) |
| I2 (102) | I2 (202) | I2 (302) | I2 (402) |
| *I3 (103) | *I3 (203) | I3 (303) | I3 (403) |
| *C (104) | *C (204) | C (304) | C (404) |
| P1 (105) | P1 (205) | P1 (305) | P1 (405) |
| P2 (106) | P2 (206) | P2 (306) | P2 (406) |
| *P3 (107) | *P3 (207) | P3 (307) | P3 (407) |
| *P4 (108) | *P4 (208) | P4 (308) | P4 (408) |
| M1 (109) | M1 (209) | M1 (309) | M1 (409) |
| M2 (110) | M2 (210) | M2 (310) | M2 (410) |

FIG. 23B

| Whole mouth average in Figures 8(*) | | | |
|---|---|---|---|
| Upper | | Lower | |
| Right | Left | Right | Left |
| I1 (101) | I1 (201) | I1 (301) | I1 (401) |
| I2 (102) | I2 (202) | I2 (302) | I2 (402) |
| I3 (103) | I3 (203) | I3 (303) | I3 (403) |
| C (104) | C (204) | C (304) | C (404) |
| *P1 (105) | *P1 (205) | P1 (305) | P1 (405) |
| *P2 (106) | *P2 (206) | P2 (306) | P2 (406) |
| *P3 (107) | *P3 (207) | P3 (307) | P3 (407) |
| *P4 (108) | *P4 (208) | P4 (308) | P4 (408) |
| M1 (109) | M1 (209) | M1 (309) | M1 (409) |
| M2 (110) | M2 (210) | M2 (310) | M2 (410) |

FIG. 23C

METHOD FOR QUANTIFYING PLAQUE IN PET ANIMALS

CROSS-REFERENCE TO RELATED APPLICATIONS

This application is Continuation of U.S. patent application Ser. No. 15/525,538, filed on May 9, 2017, which is a national stage application, filed under 35 U.S.C. § 371, of International Application No. PCT/GB2015/053464, filed Nov. 13, 2015, which claims priority from Great Britain Patent Application No. 1420273.3, filed on Nov. 14, 2014, all of which are incorporated by reference herein in their entirety for any and all purposes.

FIELD

The present invention relates to methods for detecting and quantifying the plaque levels and/or lesions in companion animals, and the use of such information during trials of oral health products. The methods disclosed enable the trialling of companion animals for a shorter period of time, without the need for long and expensive trials on oral health products to be conducted. The methods described are conducted on conscious pet animals.

BACKGROUND

The need to maintain or improve oral health in a pet animal is of great importance. Poor oral health can lead to periodontal diseases, which can have severe effects on the wellbeing of the pet animal.

It is well known that pet animals, in particular dogs and cats, suffer from periodontal diseases throughout their lives. The etiological agent in all cases of periodontal diseases is plaque. Plaque is a build-up of a bacterial biofilm. If the plaque is not removed, it hardens and forms into tartar (calculus), or it causes gingivitis, receding gums and eventually tooth loss and other periodontal diseases. Reducing or controlling bacterial build-up (plaque) in pet animals is usually accomplished by mechanical means, such as simply brushing the teeth, or supplying the pet animal with chews or pet treats, which scrape the plaque from the teeth. However, the removal of plaque by mechanical means relies on the pet animal spending sufficient time chewing the pet treat or chew and/or owner compliance regarding brushing the pet animal's teeth on a regular basis, which owners often find difficult to manage.

Once the plaque on the teeth of an animal hardens to become tartar (calculus), further plaque can accumulate, thereby reducing the effects of using mechanical means to remove the plaque and thereby leading to periodontal disease in pet animals. Such tartar (calculus) can only be removed from the teeth by a veterinarian by putting the animal under anaesthetic, which carries with it certain risks.

Typically, in pet animal oral care product testing, trials are designed to assess the efficacy of test compositions in removing and/or controlling plaque and teeth are not brushed for the duration of the trial. These trials may take up to 28 day to determine the efficacy of the test composition. The reason for this is that the effect of plaque build-up and the formation of calculus can only be clearly observed on day 28 and, as such, the efficacy of the test composition (i.e. the effectiveness in reduction of plaque and calculus build-up), is more accurate over a longer time period.

Furthermore, the pet animals usually need to be under general anaesthetic in order for a skilled human to determine the level of plaque and/or calculus on the teeth during the trial, or at a minimum, to scale and polish the teeth prior to commencing the trial.

Veterinary Oral Health Council (VOHC) provide a recommended list of teeth in cats and dogs which when product efficacy trials are conducted could be assessed to obtain a whole mouth assessment. The VOHC list of teeth is as follows:

a. Dog: Upper Jaw—I3, C, P3, P4, M1. Lower Jaw—C, P3, P4, M1 (18 teeth).

Cat: Upper Jaw—C, P3, P4. Lower Jaw—C, P3, P4, M1 (14 teeth).

| Upper | | Lower | |
|---|---|---|---|
| Right | Left | Left | Right |
| Recommended VOHC teeth (dog) | | | |
| I3 (103) | I3 (203) | | |
| C (104) | C (204) | C (304) | C (404) |
| P3 (107) | P3 (207) | P3 (307) | P3 (407) |
| P4 (108) | P4 (208) | P4 (308) | P4 (408) |
| M1(109) | M1(209) | M1(309) | M1(409) |
| Recommended VOHC teeth (cat) | | | |
| C (104) | C (204) | C (304) | C (404) |
| P3 (107) | P3 (207) | P3 (307) | P3 (407) |
| P4 (108) | P4 (208) | P4 (308) | P4 (408) |
| | | M1(309) | M1(409) |

The standard clinical method of detecting plaque and/or lesions in pet animals is to anaesthetise the pet animal and apply a dye that stains the teeth of the pet animal, in order to show the presence of plaque and/or lesions. A human scorer (who has been trained in the skill of assessing plaque/calculus build-up) then subjectively scores the coverage of the stain and the brightness of the dye to determine the level and thickness of the plaque on each tooth and determines a whole mouth assessment of plaque in the pet animal. Such methods are based on the established Logan and Boyce method. A more recent clinical method known as Gingival Contour Plaque Index (GCPI) (developed by Hills) may be performed on conscious dogs, wherein a human scorer uses a gingival contour probe to subjectively measure the length of the plaque across the gingival margin using the measuring probe to indicate the length of plaque on each and every VOHC tooth and then a whole mouth assessment can be determined for each animal.

The standard clinical method requires multiple general anaesthetics for the animals and both the standard clinical method and the GCPI method are subject to variation caused by human subjectivity. This reduces their accuracy which means a larger number of animals are needed to measure an effect than would have been the case if the method was more accurate and reproducible. In addition, the standard clinical methods described and known, use methodologies to detect the plaque and/or calculus in the subject by assessing average plaque and/or calculus in the required VOHC teeth and then obtain a whole mouth assessment.

It is therefore expensive to administer and there are limited worldwide locations where these sorts of trials can be performed.

Accordingly, there is a need for oral care product efficacy trials to be more accurate, less subjective with easily repeatable steps, without the need to anesthetize the pet animal, while still being capable of determining and evaluating plaque levels in pet animal to the high standards required to prevent and/or treat oral diseases. Further needs exist in using less highly trained humans for the scoring methods and to reduce the total number of animals to be subject to the trials.

SUMMARY

A method of determining the efficacy of a test composition in reducing or preventing oral substrate in a companion animal is provided. The method comprises
(i) obtaining one or more images of one or more teeth of a conscious companion animal at the start of the trial (day 0) using an image taking device that is capable of detecting fluorescence;
(ii) analysing the images to quantify the substrate coverage on the one or more teeth of the companion animal at the day 0;
(iii) administering the companion animal with a test composition for the duration of the trial; (iv) obtaining one or more images of the same one or more teeth of step (i) of the companion animal at pre-determined intervals during the trial;
(v) analysing the images to determine and quantify the substrate coverage and size on each tooth of the companion animal and comparing the analysis of the images taken at the start of the trial and/or at each stage of the trial; and
(vi) determining the efficacy of the test composition in reducing or preventing oral substrate in the companion animal
wherein the substrate coverage is qualitatively scored or quantified using image analysis software and wherein the companion animal has been trained to remain still for the duration of the obtaining the one or more images.

In another aspect, a method of quantifying oral substrate in a companion animal is provided. The method comprises obtaining one or more images of fewer than eighteen teeth of a conscious companion animal using an image taking device that is capable of detecting fluorescence. The images are analyzed to quantify the substrate coverage on the fewer than eighteen teeth of the companion animal. The substrate coverage is qualitatively scored or quantified using image analysis software. The companion animal has been trained to remain still for the duration of the obtaining the one or more images.

DESCRIPTION OF THE FIGURES

FIG. 21: shows the subsequent results of Variance components and diet differences for various subsets of teeth.

FIG. 22A: sets out the numbering system of teeth in dogs.

FIG. 22B: sets out the VOHC list of recommended teeth in dogs and cats.

FIG. 23A: sets out the teeth assessed in the examples of the invention and as shown in FIGS. 4 and 14.

FIG. 23B: sets out the teeth assessed in the examples of the invention and as shown in FIGS. 5, 6 and 9.

FIG. 23C: sets out the teeth assessed in the examples of the invention and as shown in FIG. 8.

DETAILED DESCRIPTION

Figure 1:
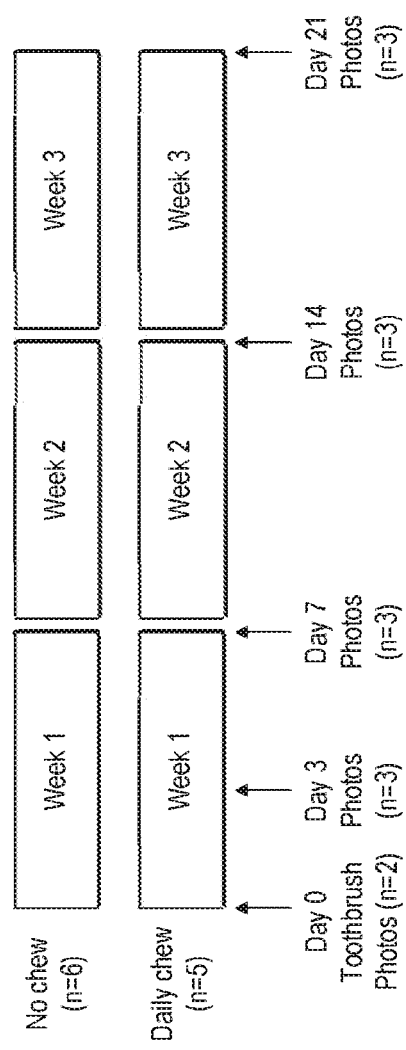
FIG. 1: Shows a representation of the trial design followed (duration of 21 days).

In the first aspect of the invention there is provided a method of detecting and quantifying oral substrate in a subject, comprising the following steps;
obtaining one or more images of one or more teeth of a conscious test subject using an image taking device that is capable of detecting fluorescence;
analysing the images; and
quantifying the substrate coverage on each tooth of each subject,
wherein the test subject is a companion animal.

The oral substrate that is detected and quantified by the method of the invention can be dental caries lesions, dental plaque, bacteria, calculus, staining, and/or any combination thereof. Preferably, the oral substrate detected is the early stages of plaque formed on the tooth.

The subject taking part in the method of the invention may be a companion animal. A companion animal can be a dog, a cat, a horse or any other such companion animal that suffers or is prone to suffer from periodontal diseases. Preferably, the companion animal is a dog or a cat.

The animal may be trained prior to step (i) in order that it remains still/static during the period of time in which the image(s) are taken. By training the animal to remain still for the length of time it takes to obtain the one or more images, a more accurate set of images can be obtained. This clearly results in a more accurate assessment of the level of plaque build-up.

The subject of the method of the invention is conscious (i.e. has not undergone anaesthetic).

The method may involve taking one or more images of the teeth in one half of the mouth of the animal, e.g. the upper half or the lower half of the mouth of the animal. The half of the mouth may be the left half or the right half. Preferably, the one or more teeth are located only in the upper half, i.e. in the upper jaw of the test animal and control animal, only. The method may involve assessing fewer than 18 teeth for dogs and fewer than 14 teeth for cats.

The substrate coverage may be in terms of the size of the area of each of the one or more teeth that fluoresces and/or the depth of the substrate as determined by the intensity of the fluorescence.

The analysis may be carried out using Qualitative Light-induced Fluorescence technology (QLF™).

In a second aspect of the invention there is provided a method of detecting and quantifying oral substrate in a subject in a trial to determine the efficacy of a test composition in reducing, preventing and/or treating oral substrate in the subject, wherein the subject is a companion animal, comprising the following steps;
obtaining one or more images of one or more teeth of a conscious test subject and a conscious control subject at the start of the trial (day 0) using an image taking device that is capable of detecting fluorescence;
analysing the images to quantify the substrate coverage on each tooth of each subject at the day 0;
administering a test composition to the test subject and a control composition to the control subject for the duration of the trial;
obtaining one or more images of the same one or more teeth of step (i) of each of the test subject and the control subject at pre-determined intervals during the trial;
analyzing the images to determine and quantify the substrate coverage and size on each tooth of each subject and comparing the images obtained at the start of the trial with the images taken at each stage of the trial;
comparing the substrate coverage of the one or more teeth of the test subject and the control subject; and
determining the efficacy of the test composition in reducing, preventing and/or treating oral substrate and/or periodontal diseases in the subject.

The test subject and the control subject may be the same subject; for example in a cross over trial design.

The method may involve taking one or more images of the teeth in one half of the mouth of the animal, e.g. the upper half or the lower half of the mouth of the animal. The half of the mouth may be the left half or the right half. Preferably, the one or more teeth are located only in the upper half, i.e. in the upper jaw of the test animal and control animal, only. The method may involve assessing fewer than 18 teeth for dogs and fewer than 14 teeth for cats.

The composition(s) used in the method of the invention can be any pet product consumed and/or administered to a companion animal. Pet products include foodstuffs, such as dry product, semi moist product, wet food product diets, liquids, as well as pet food snacks (for example, snack bars, pet chew, crunchy treat, cereal bars, snacks, biscuits and sweet products) and supplements. Food supplements can be a powder, sauce, topping, biscuit, kibble, pocket or tablet that can be administered with or without an additional foodstuff, which can be mixed with the foodstuff, sprinkled over the foodstuff or served separately or added to a liquid provided for drinking such as water or milk.

Preferably, the compositions can be a foodstuff, pet treat and/or pet chew.

The control composition can be any commercial pet food product that is a complete and balanced food which provides all the recommended vitamins and minerals for the companion animal in question, for example, as described in National Research Council, 1985, Nutritional Requirements for Dogs, National Academy Press, Washington D.C. (ISBN:0-309-03496-5); or Association of American Feed Control Officials, Official Publication 1996 and is of equivalent nutrition to the test composition, but does not have any active components or claim to have any beneficial effect in reducing, preventing and/or treating oral substrate and/or periodontal diseases in companion animals.

The test composition can be any pet food product, which has an active component and/or is considered to have a beneficial effect in reducing, preventing and/or treating oral substrate and/or periodontal diseases in companion animals.

Typically, pet product trials take up to 28 days to determine the efficacy of the test composition. The reason for this is that the effect of plaque build-up and the formation of calculus on the pet animals taking part in the trial can be more accurately observed at longer trials, for example from day 28 or onwards, thereby allowing the formation of plaque and calculus in the pet animals taking part in the trial. The method of the present invention has the advantage that the trial can be conducted in significantly shorter periods of time (from as few as 3 days) and thus preventing the formation of calculus in the pet animals taking part. This clearly contributes to the wellbeing of the pet animal subject, since plaque can be removed more easily from the teeth than calculus and maintains the oral health of animals that are given the control food product during the trial.

An important aspect of the invention is the removal of any subjectivity of the assessment which may occur with human scorers. The use of QLF™ or similar software platforms ensures that the plaque and/or calculus levels are objectively assessed and a true qualitative and/or quantitative result is obtained.

A further important aspect is the training of the animals in order that they remain still while the one or more images are being obtained. In the past, anaesthetics have been used to render the animals unconscious to obtain information on plaque build-up. However, as discussed the use of anaesthetics on companion animals carries several risks. A conscious untrained animal is very likely to move around, rendering it very difficult to obtain one or more images of the one or more teeth. In the present invention, animals may be trained prior to the obtaining of the images. The training also has the beneficial effect that the animals are not surprised or confused by the image taking and thus the stress levels of the animals are lower, contributing to their well-being.

All aspects of the first aspect apply to the second aspect of the invention, mutatis mutandis.

It is well known that some of the oral bacteria, (which form the time basis of plaque and calculus in the oral cavity of companion animals) auto-fluoresce.

Fluorescence is the emission of light that has a longer wavelength and lower energy than the absorbed radiation. Fluorescence can be detected by various means. In particular, using various light sources as excitation sources, the emission of light of a lower energy, typically, but not necessarily, visible light can be caused. The light is then detected at a given wavelength.

The method of the invention uses an image taking device that is capable of detecting fluorescence. Such devices are well known in the art.

Detection of fluorescence can be carried out using any device which detects fluorescence. The fluorescence is emitted from the surface and/or within the enamel of the tooth of the subject.

The detection of fluorescence can be achieved by any means and/or apparatus which detects light. The fluorescence can be seen visually, or through a suitable filter. The fluorescence can be detected and its intensity measured using a suitable detector and emission filter. This can be a digital camera or similar device equipped with suitable filter(s) before a CCD detector mounted in a suitable dark environment and appropriate software. The means and/or apparatus which detects light, can be visual or with specialised photographic means comprising filters which allow the fluorescence to be detected.

The image taking device is capable to detect the fluorescent radiation. The fluorescence can be detected at a wavelength of less than 800 nm, preferably less than 450 nm. Most preferably the fluorescent radiation is detected at a wavelength of 405 nm. The image taking device is capable of detecting fluorescence at a wavelength range of 300 to 800 nm, 400 to 500 nm, 350 to 700 nm or 405 to 450 nm.

The image taking device, such as a digital camera, is able to capture a first image of one or more teeth of the subject at the start of the trial (day 0) and subsequent images are taken, at pre-determined times, during the trial.

The image taken at day 0 and subsequent images taken, for example at days 3, 7, 14 and/or 21, are compared to one another and/or compared between the test and control subjects. The areas of plaque formation and/or reduction of plaque formation and/or formation of calculus and/or reduction of calculus formation during the trial are highlighted and can be qualitatively scored or quantified using image analysis software.

The fluorescence can be measured in a qualitative or quantitative manner. Present clinical scoring methods, which use skilled highly trained human scorers, determine the fluorescence or colour change of the dyes used to detect plaque on the pet animal's teeth qualitatively and/or semi-qualitatively (giving scores of 0-4). The method of the invention quantifies the substrate coverage in terms of area and depth on each tooth of each subject at the start of the trial and at each interval during the trial in order to compare the amount of plaque formation and/or reduction of plaque formation during the trial at each interval.

The present invention may use quantitative light-induced fluorescence technology (QLF™).

The analysis of the substrate in the methods of the present invention is able to assist in determining the efficacy of the test composition in reducing, preventing and/or treating oral substrate and/or periodontal diseases in the subject.

QLF™ may be used to detect the fluorescence of the plaque formed on the surface of the teeth of the companion animal. QLF™ is a relatively new method that is currently being validated for the quantification of human plaque. It uses blue and natural light to enable visualisation and subsequent quantification of plaque and calculus with or without staining agents. QLF™ relies on the auto-fluorescence of bacterial species under blue light. Images are captured in real-time using a digital camera and analyzed via image analysis software to quantify plaque and calculus coverage. Alternatively the plaque can be disclosed using standard disclosing solutions (known to those skilled in the art) to reveal more of the plaque This technique allows the user to quantify parameters like mineral loss, plaque/calculus depth, plaque/calculus size, stain size and severity with high precision and repeatability. The software analysis is able to determine the lesion area ($mm^2$), the depth of the plaque/calculus (percentage of fluorescence ($\Delta F$ in %) and volume of the lesion ($\Delta Q$ in $mm^2$).

QLF™ is a technique that is suitably used in methods for assessing plaque/calculus levels and thereby, in the inventive method of testing product efficacy in dogs. QLF™ allows rapid testing without needing to give general anesthetics to the pet animals.

The present invention also relates to (as a third aspect) the use of fluorescence in conscious dogs to determine the presence or amount of plaque and/or calculus on one or more teeth to determine the efficacy of test compositions during a trial.

All features of the first and second aspects, relate to the third aspect, mutatis mutandis.

Typically, prior to the present invention, a trial period of up to 28 days was required to determine the effect of the test composition on calculus of the subjects. In contrast, for a trial to determine the efficacy against plaque, the present invention has determined that a trial period may be as few as 3 days, 5 days or 7 days.

The method of the present invention is conducted in a trial period of up to 14 days. In some embodiments, the trial period is at least 7 days. In some embodiments, the trial period is between 3 to 7 days.

The method of this invention is able to accurately measure the progression of plaque formation in conscious pet animals.

The method thus enables accurate plaque and/or calculus detection to be carried out over a shorter period, such as 3, 4, 7, 14 or 21 days, than previous methods known in the art.

The present invention is able to provide a quick, accurate determination of whether plaque and/or calculus is present on one or more teeth without the subject being anaesthetised.

A fourth aspect of the invention is a method of detecting and quantifying oral substrate in a cat, by using QLF™. The cat can be conscious or unconscious.

In the fourth aspect of the invention there is provided a method of detecting and quantifying oral substrate in a cat, comprising the following steps;
  obtaining one or more images of one or more teeth in a cat using an image taking device that is capable of detecting fluorescence;
  analysing the images; and
  quantifying the substrate coverage on each tooth of the cat.

The oral substrate that is detected and quantified can be dental caries lesions, dental plaque, bacteria, calculus, staining, and/or any combination thereof. Preferably, the oral substrate detected is plaque in the early stages of development on the tooth.

The method may involve taking one or more images of the teeth in one half of the mouth of the cat, e.g. the upper half or the lower half of the mouth of the cat. The half of the mouth may be the left half or the right half. Preferably, the one or more teeth are located only in the upper half, i.e. in the upper jaw of the test cat and control cat only. The method may involve assessing fewer than 14 teeth in the cat's mouth.

The substrate coverage may be in terms of the size of the area of each of the one or more teeth that fluoresces and/or the depth of the substrate as determined by the intensity of the fluorescence.

The analysis is carried out using Qualitative Light-induced Fluorescence technology (QLF™).

In a fifth aspect of the invention there is provided a method of detecting and quantifying oral substrate in a cat in a trial to determine the efficacy of a test composition in reducing, preventing and/or treating oral substrate in a cat, comprising the following steps;
  obtaining one or more images of one or more teeth in a cat as the test subject and a control cat at the start of the trial (day 0) using an image taking device that is capable of detecting fluorescence;
  analysing the images to quantify the substrate coverage on each tooth of each subject at the day 0;
  administering a test composition to the test subject and a control composition to the control subject for the duration of the trial;
  obtaining one or more images of the same one or more teeth of step (i) of each of the test cat and the control cat at pre-determined intervals during the trial;
  analyzing the images to determine and quantify the substrate coverage and size on each tooth of each subject and comparing the images obtained at the start of the trial with the images taken at each stage of the trial;
  comparing the substrate coverage of the one or more teeth of the test cat and the control cat; and
  determining the efficacy of the test composition in reducing, preventing and/or treating oral substrate and/or periodontal diseases in the cat.

The test cat and the control cat may be the same cat; for example in a cross over trial design.

The cat can be conscious or unconscious.

The method may involve taking one or more images of the teeth in one half of the mouth of the cat, e.g. the upper half or the lower half of the mouth of the cat. The half of the mouth may be the left half or the right half. Preferably, the one or more teeth are located only in the upper half, i.e. in the upper jaw of the test cat and control cat only. The method may involve assessing fewer than 14 teeth in the cat's mouth.

The composition(s) used in the method of the invention can be any pet product consumed and/or administered to a cat. Pet products include foodstuffs, such as dry product, semi moist product, wet food product diets, liquids, as well as pet food snacks (for example, snack bars, pet chew, crunchy treat, cereal bars, snacks, biscuits and sweet products) and supplements. Food supplements can be a powder, sauce, topping, biscuit, kibble, pocket or tablet that can be administered with or without an additional foodstuff, which can be mixed with the foodstuff, sprinkled over the foodstuff or served separately or added to a liquid provided for drinking such as water or milk.

Preferably, the composition (s) can be a foodstuff, pet treat and/or pet chew.

The control composition can be any commercial cat food product that is a complete and balanced food which provides all the recommended vitamins and minerals for the cat in question and is of equivalent nutrition to the test composition, but does not have any active components or claim to have any beneficial effect in reducing, preventing and/or treating oral substrate formation and/or periodontal diseases in cats.

The test composition can be any cat food product, which has an active component and/or is considered to have a beneficial effect in reducing, preventing and/or treating oral substrate formation and/or periodontal diseases in cats.

An important aspect of the invention is the removal of any subjectivity of the assessment which may occur with human scorers. The use of QLF™ or similar software platforms ensures that the plaque and/or calculus levels are objectively assessed and a true qualitative and/or quantitative result is obtained.

All aspects of the fourth aspect apply to the fifth aspect of the invention, mutatis mutandis.

The method of the invention uses an image taking device that is capable of detecting fluorescence. Such devices are well known in the art.

Detection of fluorescence can be carried out using any device which detects fluorescence. The fluorescence is emitted from the surface and/or within the enamel of the tooth of the subject.

The detection of fluorescence can be achieved by any means and/or apparatus which detects light. The fluorescence can be seen visually, or through a suitable filter. The fluorescence can be detected and its intensity measured using a suitable detector and emission filter. This can be a digital camera or similar device equipped with suitable filter(s) before a CCD detector mounted in a suitable dark environment and appropriate software. The means and/or apparatus which detects light, can be visual or with specialised photographic means comprising filters which allow the fluorescence to be detected.

The image taking device is capable to detect the fluorescent radiation. The fluorescence can be detected at a wavelength of less than 800 nm, preferably less than 450 nm. Most preferably the fluorescent radiation is at a wavelength of 405 nm. The image taking device is capable of detecting fluorescence at a wavelength range of 300 to 800 nm, 400 to 500 nm, 350 to 700 nm or 405 to 450 nm.

The image taking device, such as a digital camera, is able to capture a first image of one or more teeth of the subject at the start of the trial (day 0) and subsequent images are taken, at pre-determined times, during the trial.

The image taken at day 0 and subsequent images taken, for example at days 3, 7, 14 and/or 21, are compared to one another and/or compared between the test and control subjects. The areas of plaque formation and/or reduction of plaque formation and/or formation of calculus and/or reduction of calculus formation during the trial are highlighted and can be qualitatively scored or quantified using image analysis software.

The detection of fluorescence can be measured in a qualitative or quantitative manner. Present clinical scoring methods, which use skilled highly trained human scorers, determine the fluorescence or colour change of the dyes used to detect plaque on the pet animal's teeth qualitatively and/or semi-qualitatively (giving scores of 0-4). The method of the invention quantifies the substrate coverage in terms of area and depth on each tooth of each subject at the start of the trial and at each interval during the trial in order to compare the amount of plaque formation and/or reduction of plaque formation during the trial at each interval.

The present invention may use quantitative light-induced fluorescence technology (QLF™).

The analysis of the substrate in the methods of the present invention is able to assist in determining the efficacy of the test composition in reducing, preventing and/or treating oral substrate and/or periodontal diseases in the cats.

QLF™ may be used to detect the fluorescence of the plaque formed on the surface of the teeth of the companion animal. QLF™ is a relatively new method that is currently being validated for the quantification of human plaque. It uses blue and natural light to enable visualisation and subsequent quantification of plaque and calculus with or without staining agents. QLF™ relies on the auto-fluorescence of bacterial species under blue light. Images are captured in real-time using a digital camera and analyzed via image analysis software to quantify plaque and calculus coverage. Alternatively the plaque can be disclosed using standard disclosing solutions (known to those skilled in the art) to reveal more of the plaque This technique allows the user to quantify parameters like mineral loss, plaque/calculus depth, plaque/calculus size, stain size and severity with high precision and repeatability. The software analysis is able to determine the lesion area ($mm^2$), the depth of the plaque/calculus (percentage of fluorescence ($\Delta F$ in %) and volume of the lesion ($\Delta Q$ in $mm^2$).

QLF™ is a technique that is suitable to be used in methods for assessing plaque/calculus levels and thereby, in the inventive method of testing product efficacy in cats.

The present invention enables accurate assessment of plaque and/or calculus build-up of the mouth of the animal using images from one or more teeth from the mouth, from one or more teeth from the upper or lower jaw of the mouth, one or more teeth from either the lower or upper right side of the jaw or from the lower or upper left side of the jaw of the mouth of the animal being tested or combinations thereof (for example, half mouth (upper/lower jaw, right/left side of the jaw) or quarter mouth analysis In particular, the invention has the advantage that it is able to determine the amount of plaque and/or calculus in the mouth of the test animal, by simply detecting the amount of plaque and/or calculus in one or more teeth of the upper jaw of the mouth and accurately correlating the amount of plaque and/or calculus in the entire mouth of the animal being tested, and/or detecting the amount of plaque and/or calculus in one or more teeth of the upper jaw of the mouth to detect difference between control and tests group The method is capable of assessing fewer than 18 teeth for dogs and fewer than 14 teeth for cats to determine a whole mouth assessment. The method can assess fewer than 18, 17, 16, 15, 14, 13, 12, 11, 10, 9, 8, 7, 6, 5, 4, 3, 2 teeth or an individual tooth in dogs to determine the whole mouth assessment. The method can assess fewer than 14, 13, 12, 11, 10, 9, 8, 7, 6, 5, 4, 3, 2 teeth or an individual tooth in cats to determine the whole mouth assessment. This provides an advantage to the prior known methods as not only is the present invention able to be carried out in conscious pet animals, it is capable of providing trial results in shorter time frames (3, 7, 14, 21 days as opposed to 28 days) and is also able to determine the amount of plaque and/or calculus in the entire mouth of an animal subject by measuring the fluorescence of one or more teeth of the upper or lower jaw of the mouth, one or more teeth from either the lower or upper right side of the jaw or from the lower or upper left side of the jaw of the mouth or combinations thereof. The present invention determines a faster and more reliable methodology to the pet industry.

The invention will now be further described by way of reference to the following Examples which are provided for the purposes of illustration only and are not to be construed as being limiting on the invention.

EXAMPLES

The following examples show methods used to validate the use of Quantitative Light-induced Fluorescence (QLF™) for quantifying plaque levels in animals by assessing its repeatability, reproducibility and accuracy and comparing it to an established clinical scoring system. Trials were performed using dogs to determine (i) Intra-photographer repeatability, (ii) inter-photographer reproducibility and (iii) comparison with current scoring method, as well as evidencing a 7 day trial with conscious dogs and using the methodology in cats.

Example 1: Intra-Photographer Repeatability

The aim of this example was to determine the intra-photographer repeatability when measuring plaque coverage of dog's teeth using QLF™.

A panel size of 11 miniature schnauzer dogs aged between 2.5 and 6.9 years was selected. The dogs all had received a recent scale and polish (within the last month) and had little or no visible calculus. Dogs were tooth brushed daily for approximately one week prior to the start of the trial and were last tooth brushed on day one of the trial prior to their baseline measurement. Dogs received no subsequent tooth brushing for the three week (21 days) duration of the trial. All dogs during the trial were conscious.

The trial phase of 3 weeks (21 days) was determined to be long enough to allow the build-up of high levels of plaque. Dogs were fed a mixed wet and dry diet during the trial and the test group were given a chew on a daily basis (chew vs. no chew).

Images of undisclosed teeth were captured QLF™ by a single photographer on days 1, 3, 7, 14 and 21. Three repeat images, two in the morning and one in the afternoon, were taken on days 3, 7, 14 and 21 and two on day 1 (see FIG. 1). Taking images on all these days gave a range of different plaque coverages which was important for assessing the intra-photographer variability across the range.

Measures were obtained by taking four images of the upper jaw capturing teeth numbers 103-108 and 203-208. See FIG. 2.

Figure 2:
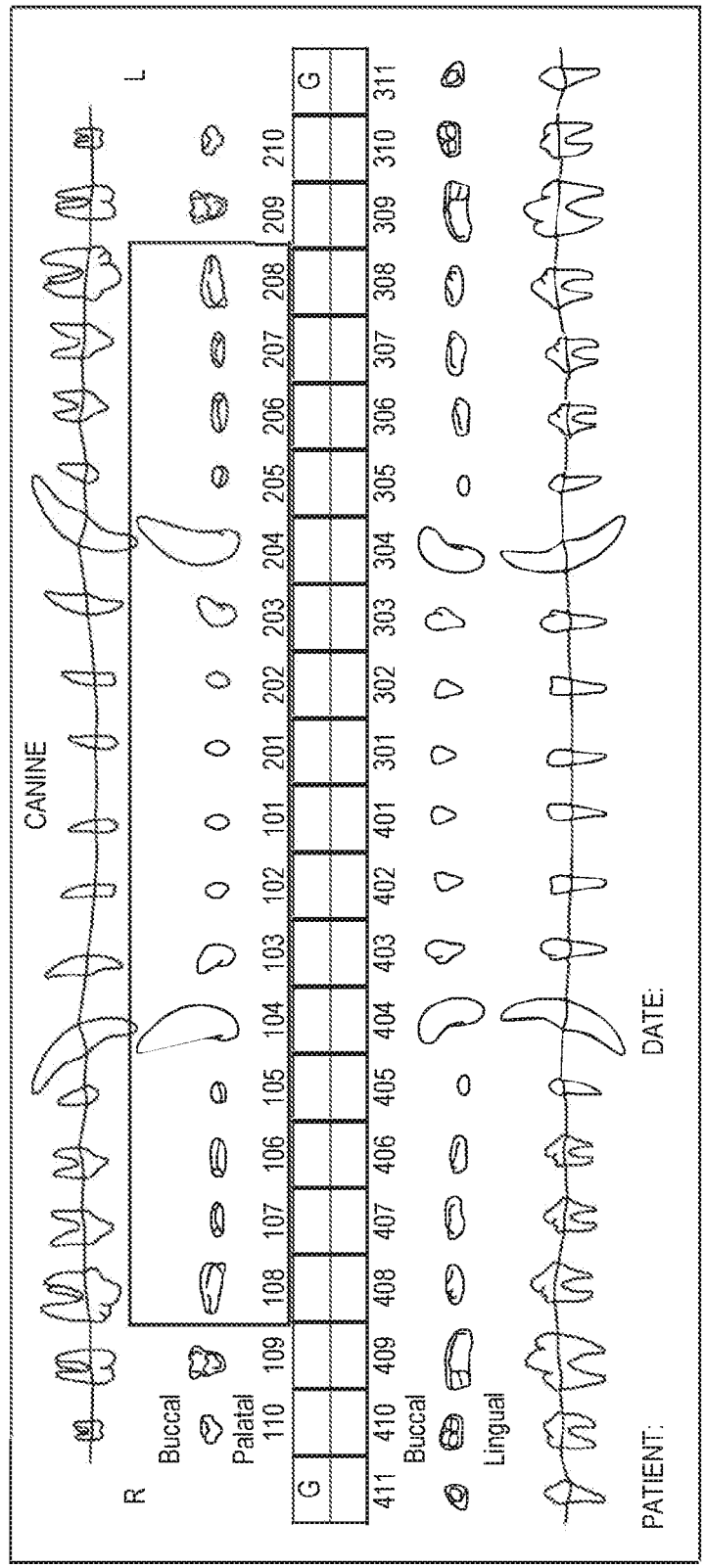
FIG. 2: Shows a representation of a dog's entire mouth (upper and lower jaw) and the respective numerical system used for labelling the teeth in the mouth.

FIG. 2: Shows a representation of a dog's entire mouth (upper and lower jaw) and the respective numerical system used for scoring the teeth in the mouth. It is known that VOHC clinical scoring methods requires teeth to be scored from maxillary 03, 04, 07, 08, 09 and mandibular 04, 07, 08, 09. The amount of plaque coverage was measured across teeth numbers 101 to 108 and 201 to 208 (as indicated).

To reduce the effects of muscle memory on the positioning of the camera for imaging, the trial was designed so that the examiner imaged all the dogs in succession and then went back to the first dog and imaged them all again for the repeat set. After lunch the third set of images were then taken. This meant that the time between the 3 images was about 1 hour between images 1 and 2 and was about 1½ hours between images 2 and 3.

A set of images comprised five views around the mouth; two images on both the left hand side and right hand side of the dog's mouth were taken to visualise the maxilla $1^{st}$ premolars (P1; 105, 205), $2^{nd}$ premolars (P2; 106, 206), $3^{rd}$ premolars (P3; 107, 207) and $4^{th}$ premolars (P4; 108, 208) and one image from the front to visualise the maxilla and mandibular $1^{st}$ incisors (I1; 101, 201, 301, 401), $2^{nd}$ incisors (I2; 102, 202, 302, 402), $3^{rd}$ incisors (I3; 103, 203, 303, 403) and part of the canines (C; 104, 204, 304, 404). See FIG. 2.

| Teeth set of images | Teeth numbers assessed by the images taken |
|---|---|
| Maxilla $1^{st}$ premolars (P1) | 105, 205 |
| $2^{nd}$ Premolars (P2) | 106, 206 |
| $3^{rd}$ Premolars (P3) | 107, 207 |
| $4^{th}$ Premolars (P4) | 108, 208 |
| Maxilla and $1^{st}$ Incisors (I1) | 101, 201, 301, 401 |
| $2^{nd}$ Incisors (I2) | 102, 202, 302, 402 |
| $3^{rd}$ Incisors (I3) | 103, 203, 303, 403 |
| Part of canines (C) | 104, 204, 304, 404 |

Statistics

Linear mixed effects models (REML) were used to estimate variance components of the percentage plaque coverage. First a model including all teeth, using repeat nested within time nested within tooth nested within dog as the fitted random effects and then secondly for each tooth type, using repeat nested within time nested within dog. The percentage variability accountable to repeatability and the percentage coefficient of variability (repeatability standard deviation relative to the overall mean of the model) were then calculated.

Results

Figure 3:
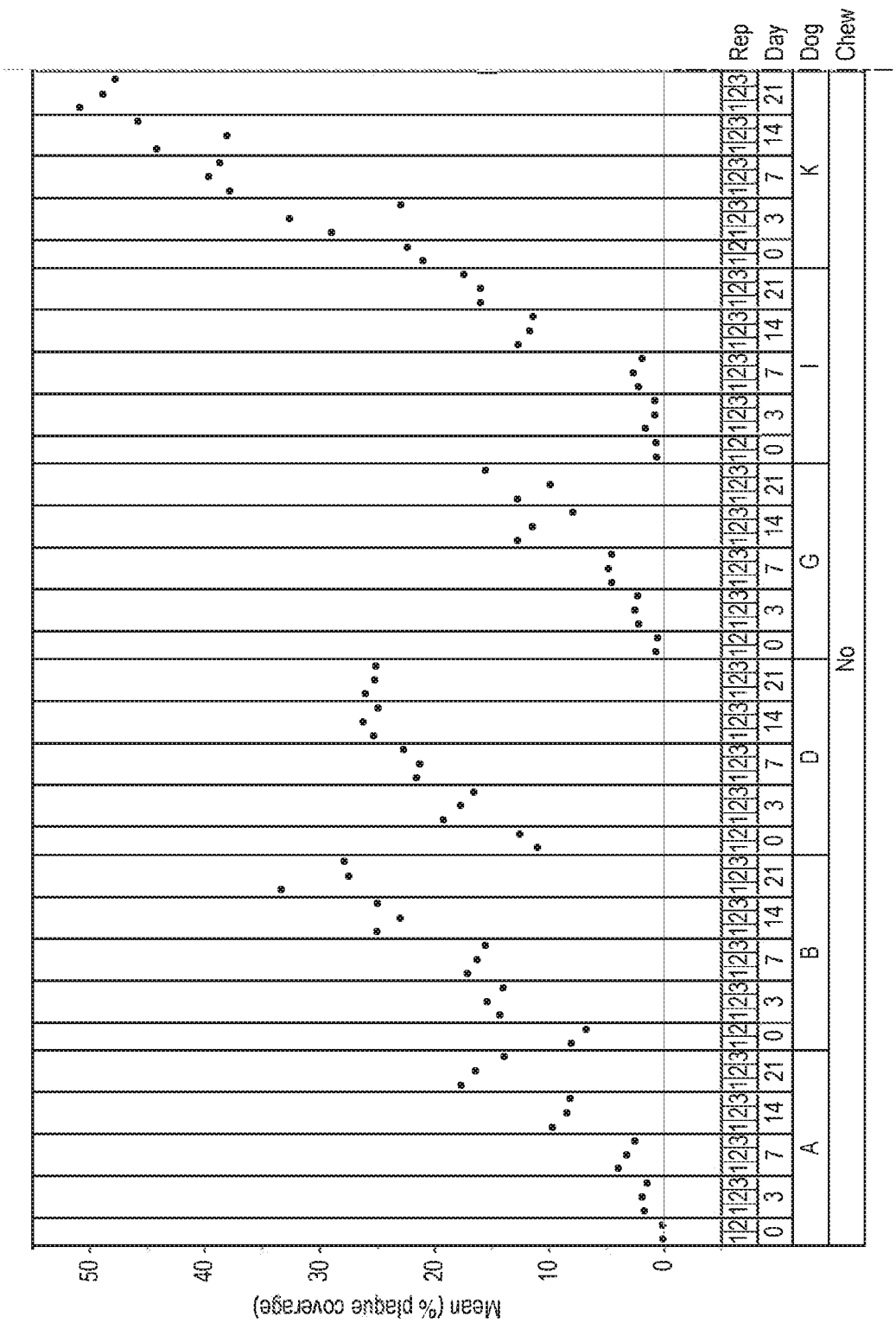
FIG. 3: Shows the average mouth results of the percentage plaque coverage per dog per day.
Figure 3:
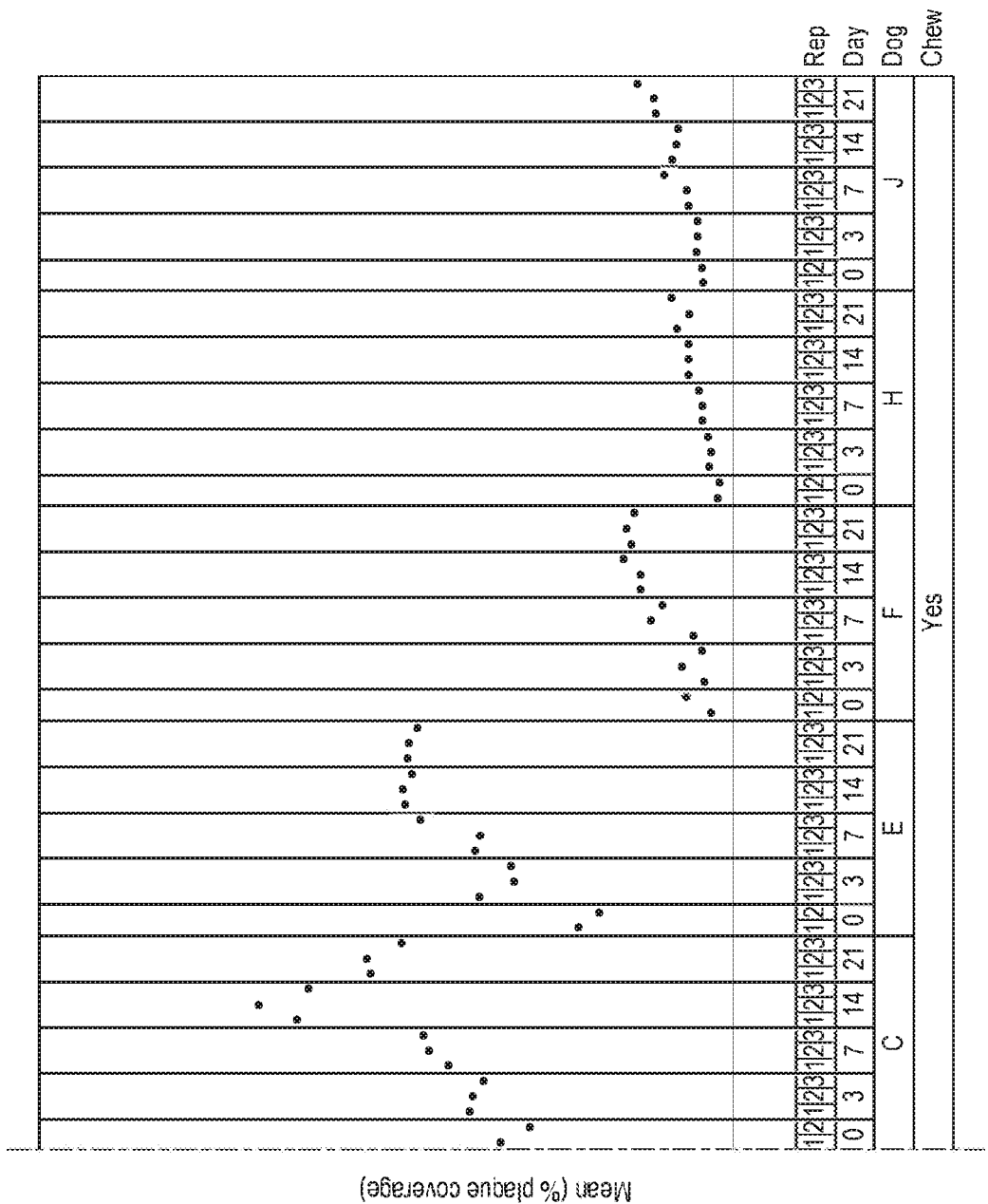
Figure 4:
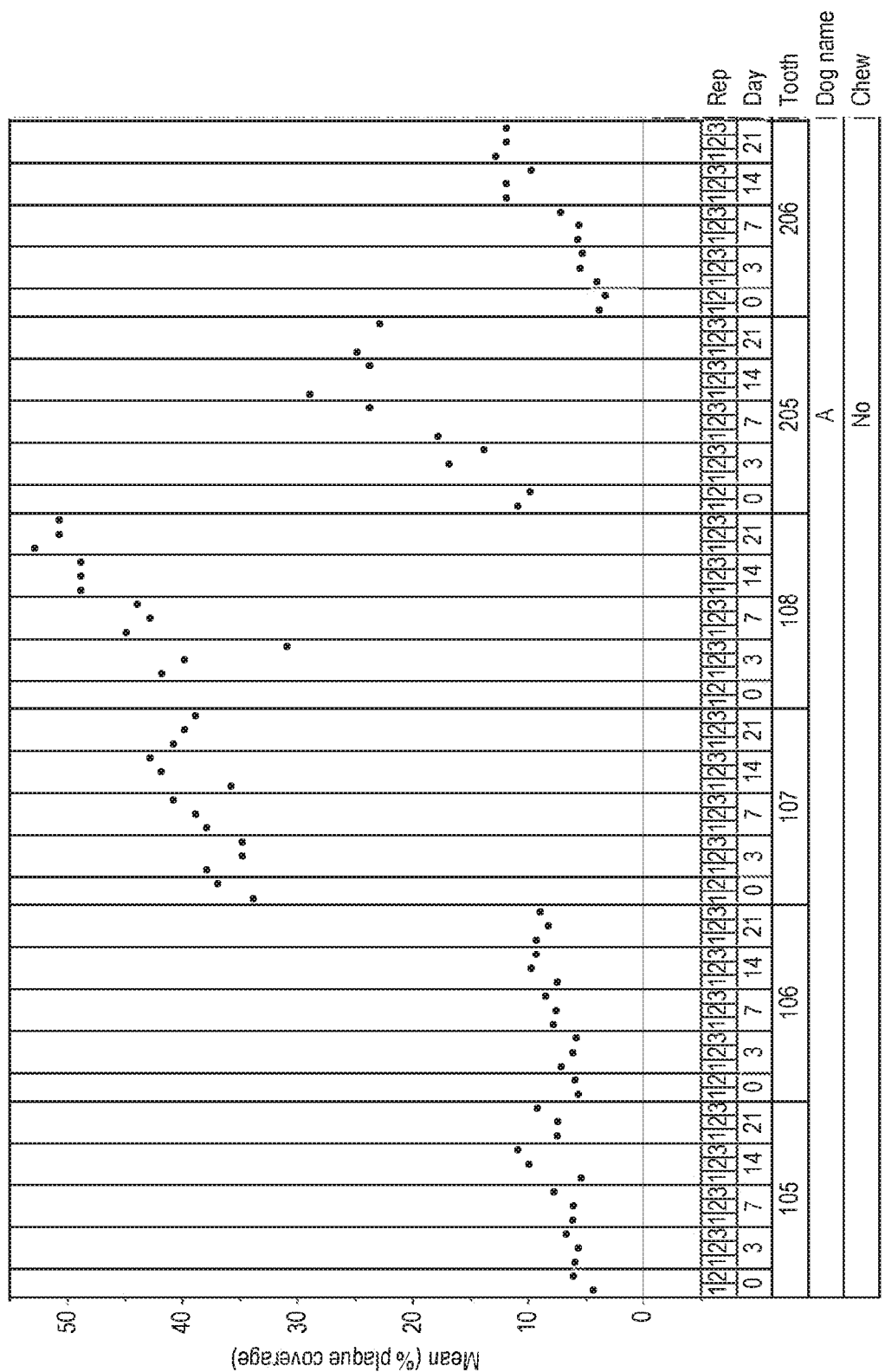
FIG. 4: Shows the individual teeth results of the percentage plaque coverage per tooth over time for each repeat for two example dogs.
Figure 4:
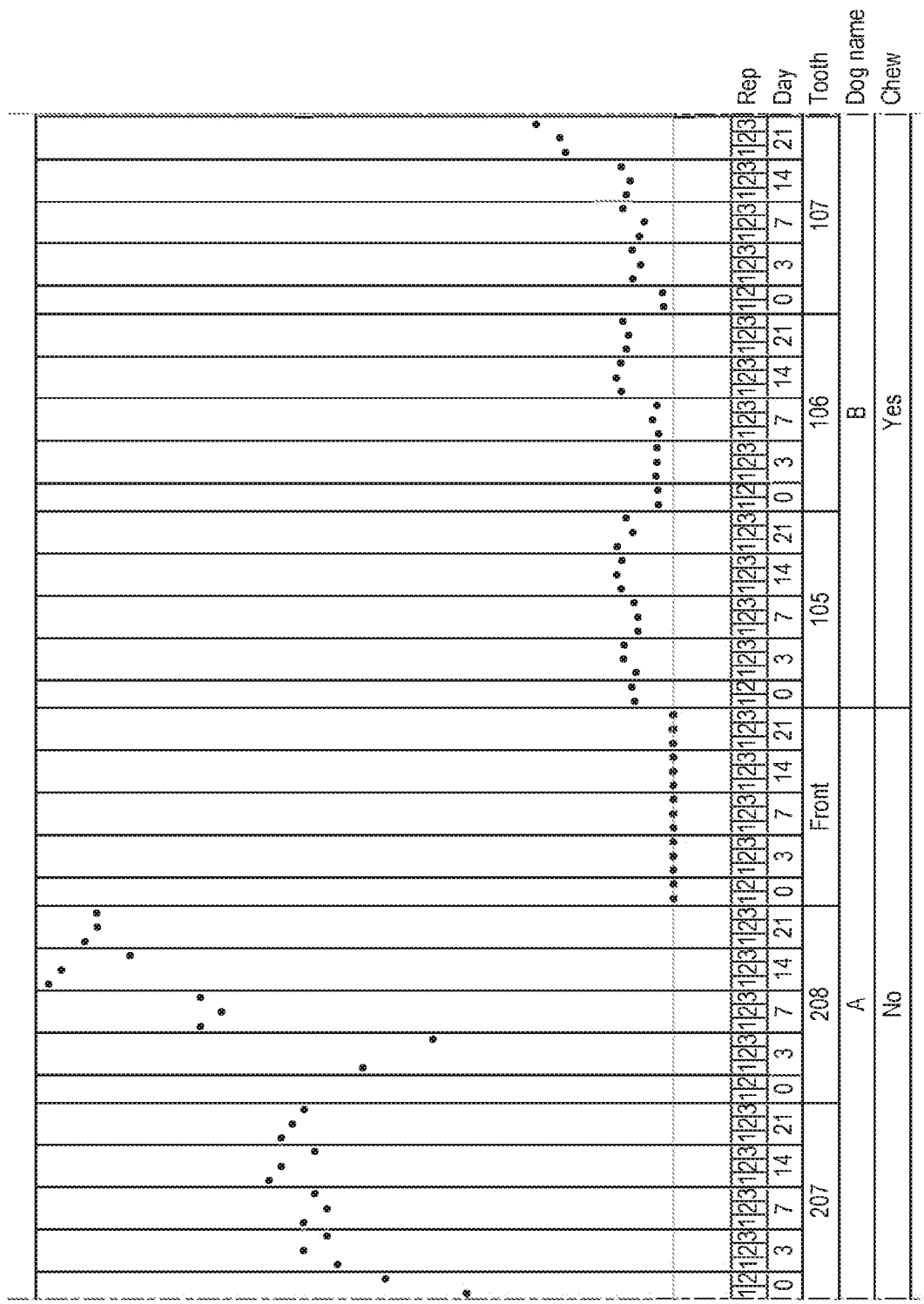
Figure 4:
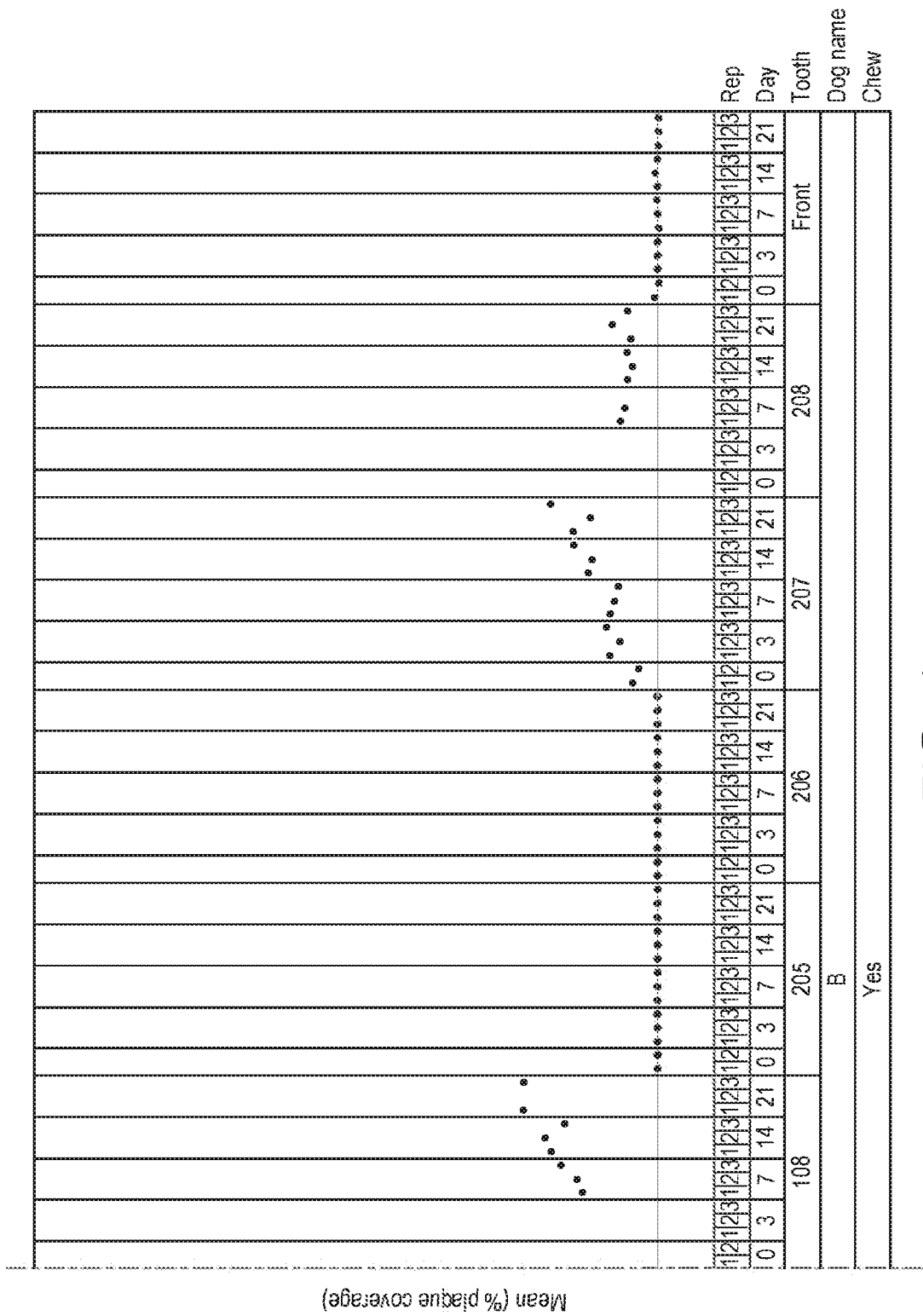

Images of 1584 undisclosed maxillary teeth (P1, P2, P3, P4) and 198 front views (single image capturing I1, I2, I3 and part of canine) from eleven miniature schnauzers were analyzed using QLF™ image analysis software to quantify plaque coverage (FIGS. 3 and 4).

FIG. 3: Shows the mean percentage plaque coverage for 11 dogs (A-K) receiving a chew compared to no chew. Three sets of images (1-3) were acquired on days 0, 3, 7, 14 & 21. Measures of percentage plaque coverage were obtained from the computerised images for teeth 105, 106, 107, 108, 205, 206, 207 and 208 individually and collectively and for front teeth (101, 102, 103, partial 104, 201, 202, 203 and partial 204). This study demonstrates that images of teeth can be obtained in conscious dogs and that the amount of plaque accumulation can be measured over a 3-21 day time-frame. It can also be seen that dogs that received a chew generally had lower levels of plaque than dogs that received no chew.

Variance components analysis was used to quantify the intra-photographer repeatability across days, teeth and dogs. The repeatability coefficient of variation (100*standard deviation relative to the mean plaque coverage) for the maxillary premolars was 7.5%.

The repeatability component of variability was also calculated for each tooth, across days and dogs (see table 2 and FIG. 4).

FIG. 4: Shows an example of the percentage plaque coverage for each of the maxillary premolars (105 to 108 and 205 to 208) and the front teeth (mean of maxillary and mandibular incisors and partial canines) overtime (days 0, 3, 7, 14, 21) for two dogs and the three repeat sets of images (1-3). QLF™ enables the analysis of plaque coverage in individual teeth over time which is of great benefit for products targeted to specific teeth.

The QLF™ method showed good repeatability with the majority of teeth assessed accounting for <1.4% of the total variability in the data, with the exception of tooth 206 (5.2%) and the front teeth (27.9%). Making the variance components relative to the tooth means showed that the percentage coefficient of variation (% CV) ranged from 6% to 16% for most of the teeth analyzed with the exception of 206 (30%) and the front teeth (79%). These teeth had the lowest average percentage plaque coverage, 7.7% and 0.68% for tooth 206 and front teeth respectively which may have contributed to the increased relative variability. However, the high % CV on these teeth is of little consequence if using this technique to support product efficacy claims as the P3 and P4 were the only teeth evaluated in this trial that are required by the VOHC for claims validation trials and QLF™ showed the highest repeatability on these teeth with % CVs of <9%. By comparison Modified L&B repeatability is estimated to be >29% based on the info from Hennet et al. 2006.

TABLE 2

Variability and % CV for eight individual teeth and the front teeth

| Tooth | Variance Component | SD | % Variability | Mean | % CV |
|---|---|---|---|---|---|
| 105 | 2.02 | 1.42 | 0.87 | 9.643 | 14.74 |
| 106 | 1.85 | 1.36 | 1.36 | 9.597 | 14.16 |
| 107 | 2.91 | 1.71 | 0.83 | 25.77 | 6.62 |
| 108 | 3.18 | 1.78 | 0.69 | 28.73 | 6.20 |
| 205 | 2.60 | 1.61 | 1.13 | 10.29 | 15.68 |
| 206 | 5.04 | 2.24 | 6.19 | 7.386 | 30.39 |
| 207 | 3.53 | 1.88 | 0.94 | 20.83 | 9.02 |
| 208 | 6.24 | 2.50 | 1.54 | 20.47 | 12.20 |
| Front | 0.29 | 0.54 | 28.47 | 0.6535 | 81.98 |

One of the objectives of this trial was to assess how to use the technique. In subsequent trials, the front teeth were not imaged and more images were taken from the side to ensure all VOHC teeth were photographed (where visible).

In summary, this study showed that images can be acquired of the maxillary teeth in conscious dogs. QLF™ is repeatable and the changes in the quantities of plaque can be measured over time frames of between 3 and 21 days. The levels of plaque coverage can be determined for individual teeth, which is beneficial for products targeted at specific teeth.

Example 2: Inter-User Reproducibility

The aim of this example was to evaluate the reproducibility between five photographers when measuring plaque coverage in conscious dogs using QLF™.

Figure 5:
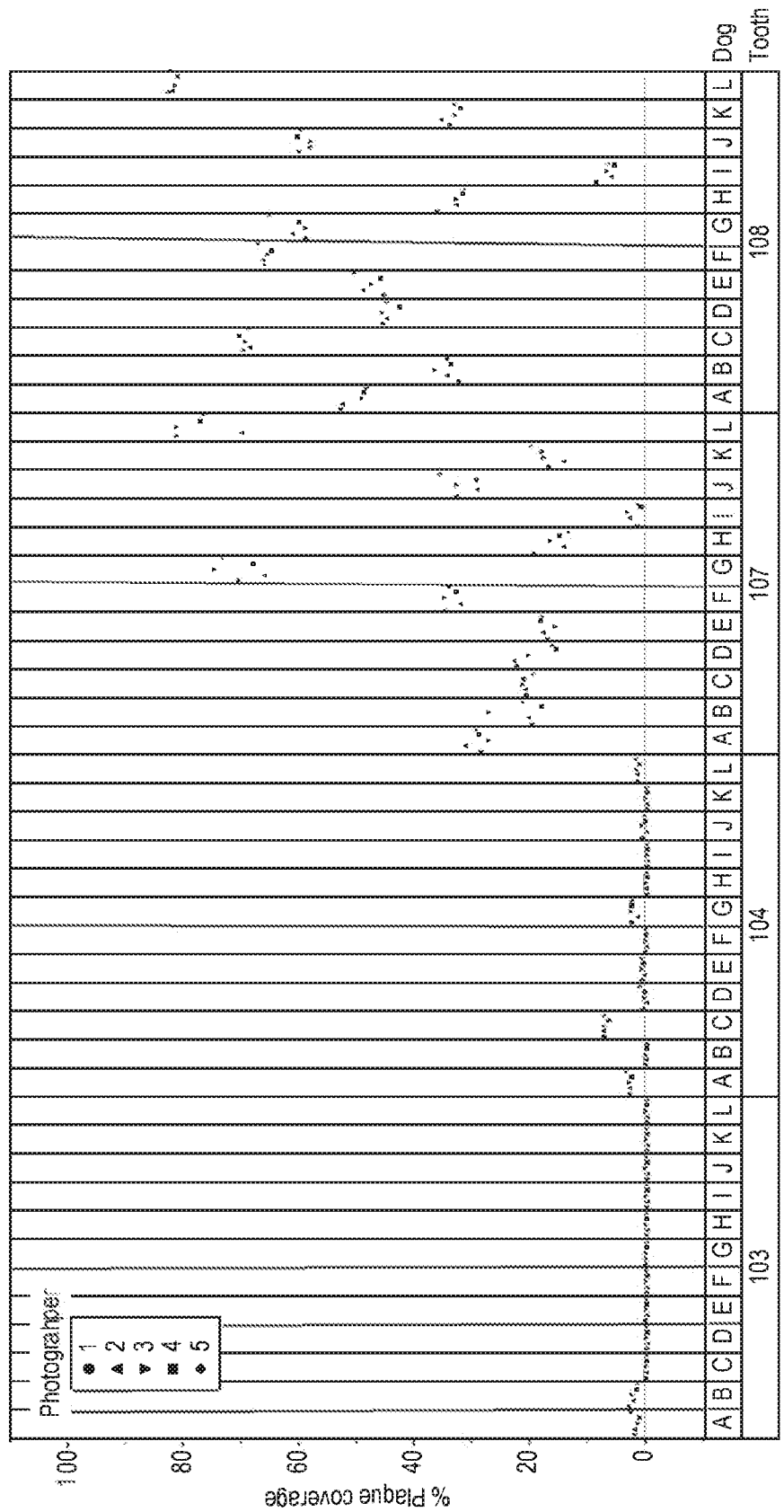
FIG. 5: Shows the reproducibility of undisclosed individual teeth results for 103 to 108 evidencing the percentage plaque coverage by tooth, dog and photographer.

Five photographers took images of teeth in conscious miniature schnauzers (N=12) fed on the same dry diet. Dogs were tooth brushed every other day prior to the start of trial. Tooth brushing was ceased 1, 10 and 21 days prior to images being taken to assess different levels of plaque and calculus. Images were taken of teeth 103-108 and 203-208 by each photographer within a 2 hour period (FIG. 5).

Linear mixed models (REML) were used to estimate variance components of the percentage plaque coverage, with photographer nested in dog as the random effects. The percentage variability accountable to the photographer and the % CV (reproducibility standard deviation relative to the overall mean of the model) were then calculated.

Figure 6:
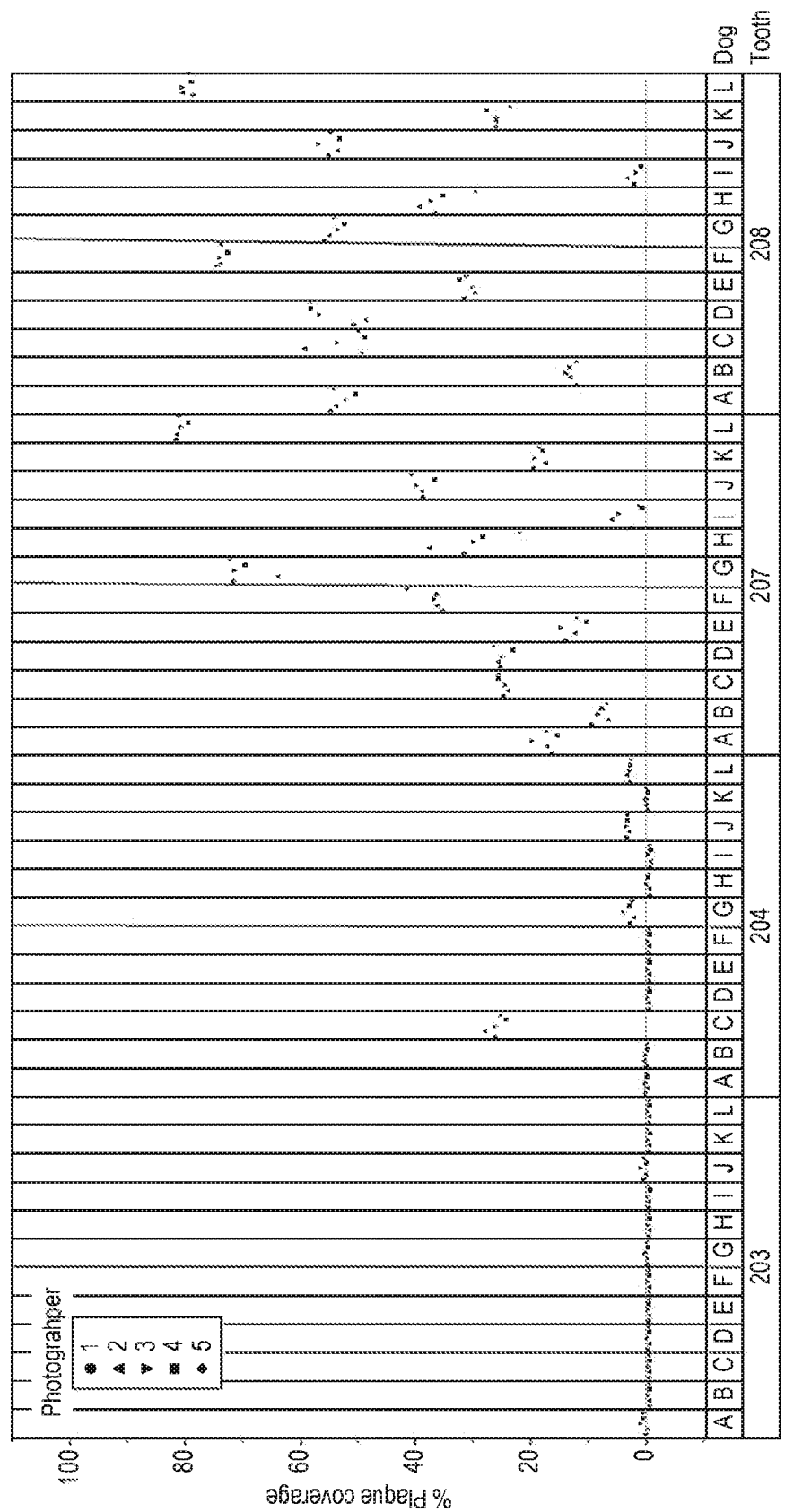
FIG. 6: Shows the reproducibility of undisclosed individual teeth results for 203 to 208 evidencing the percentage plaque coverage by tooth, dog and photographer.

The percentage plaque coverage was determined for 480 undisclosed maxillary teeth (I3, C, P3 and P4), 96 per photographer. The teeth selected were based on the teeth scored using the modified Logan & Boyce method, as defined by the VOHC standard product testing protocols. FIGS. 5 and 6: Shows the percentage plaque coverage of individual teeth (FIG. 5 shows 103 to 108 teeth and FIG. 6 shows teeth 203 to 208) for 12 dogs (A-L) and 5 photographers (1-5). The coefficient of variation (deviation relative to mean % plaque coverage) for an average tooth was 10.9% CV. This data shows that QLF™ can be used to reproducibly measure the quantity of plaque on individual teeth.

Figure 7:
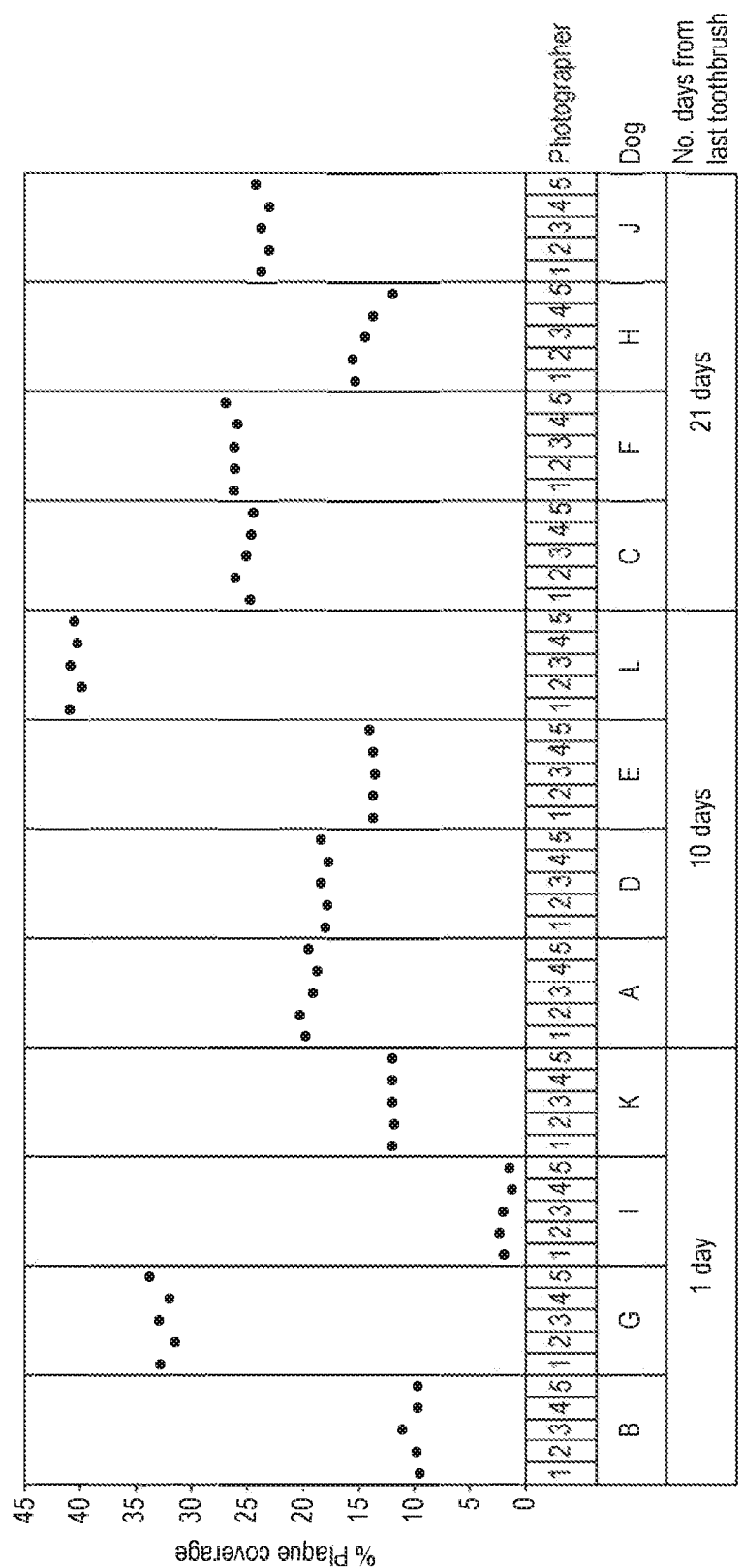
FIG. 7: Shows the percentage plaque coverage (whole mouth average: 13, C, P3, P4) as determined by QLF™ on undisclosed teeth per day, by dog and photographer.

The mouth averages ranged from 1.2% to 41.2% plaque coverage (FIG. 7) and the inter-photographer reproducibility coefficient of variability for a mouth average was 3.21%. FIG. 7: Percentage plaque coverage (whole mouth average: I3, C, P3, P4) as determined by QLF™ on undisclosed teeth, by dog and examiner. The figure shows the reproducibility of average plaque coverage from five photographers (1-5) taking images of 12 dogs (A-L). The variation relative to the mean percentage coverage (% CV) between the different photographers was 3.2%. As compared to standard Modified Logan & Boyce (Based on Hennet et al., 2006) having 8.8% CV.

In summary, QLF™ is reproducible and the percentage plaque coverage can be measured in the individual teeth on the maxillary jaw in conscious dogs. The amount of plaque can be quantified at 1, 10 and 21 days after stopping tooth brushing.

Figure 8:
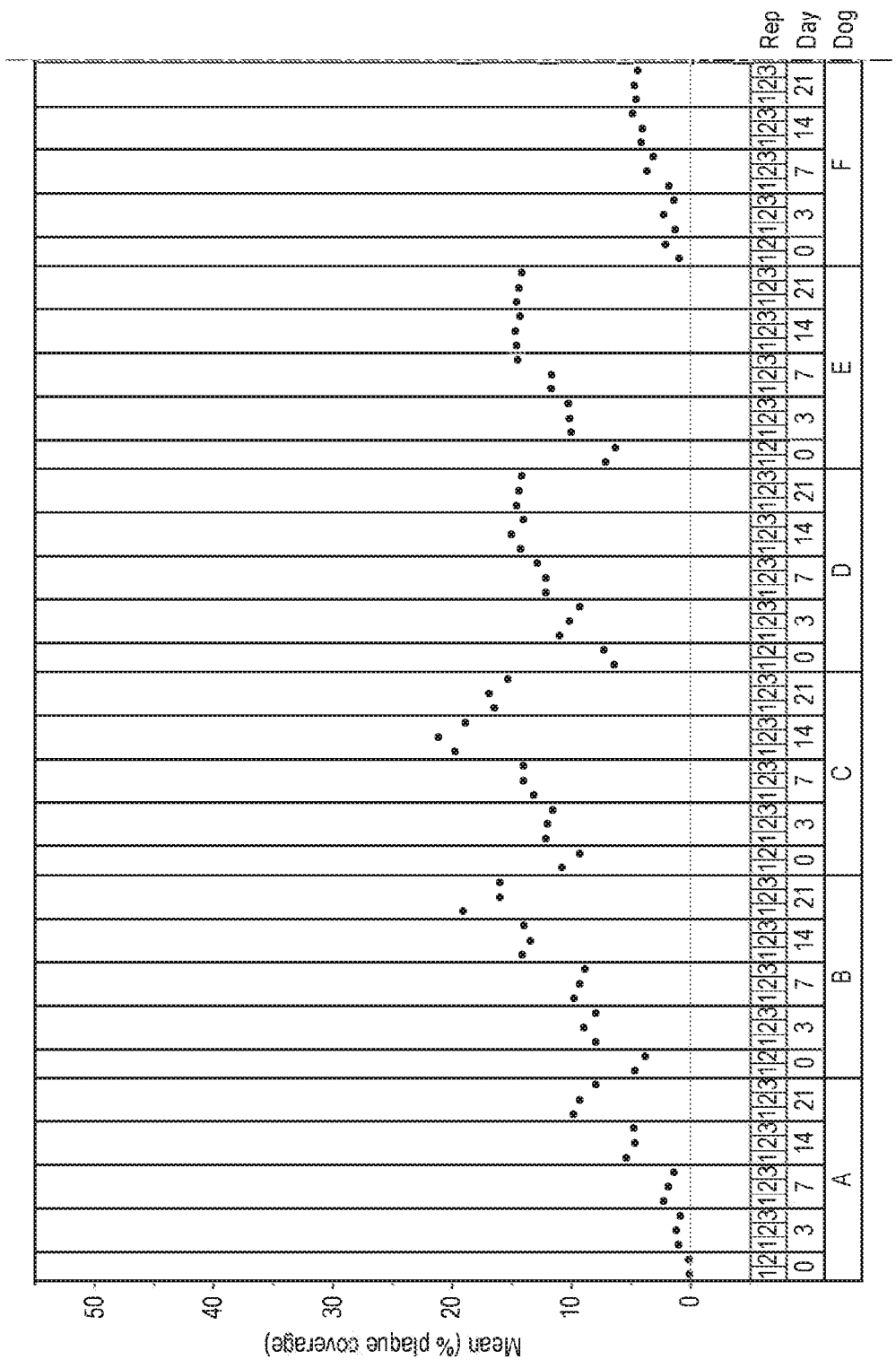
FIG. 8: Variability plot of percentage plaque coverage (whole mouth average including maxillary P1, P2, P3, P4), as determined by QLF™ on undisclosed teeth by dog, day and repetition.
Figure 8:
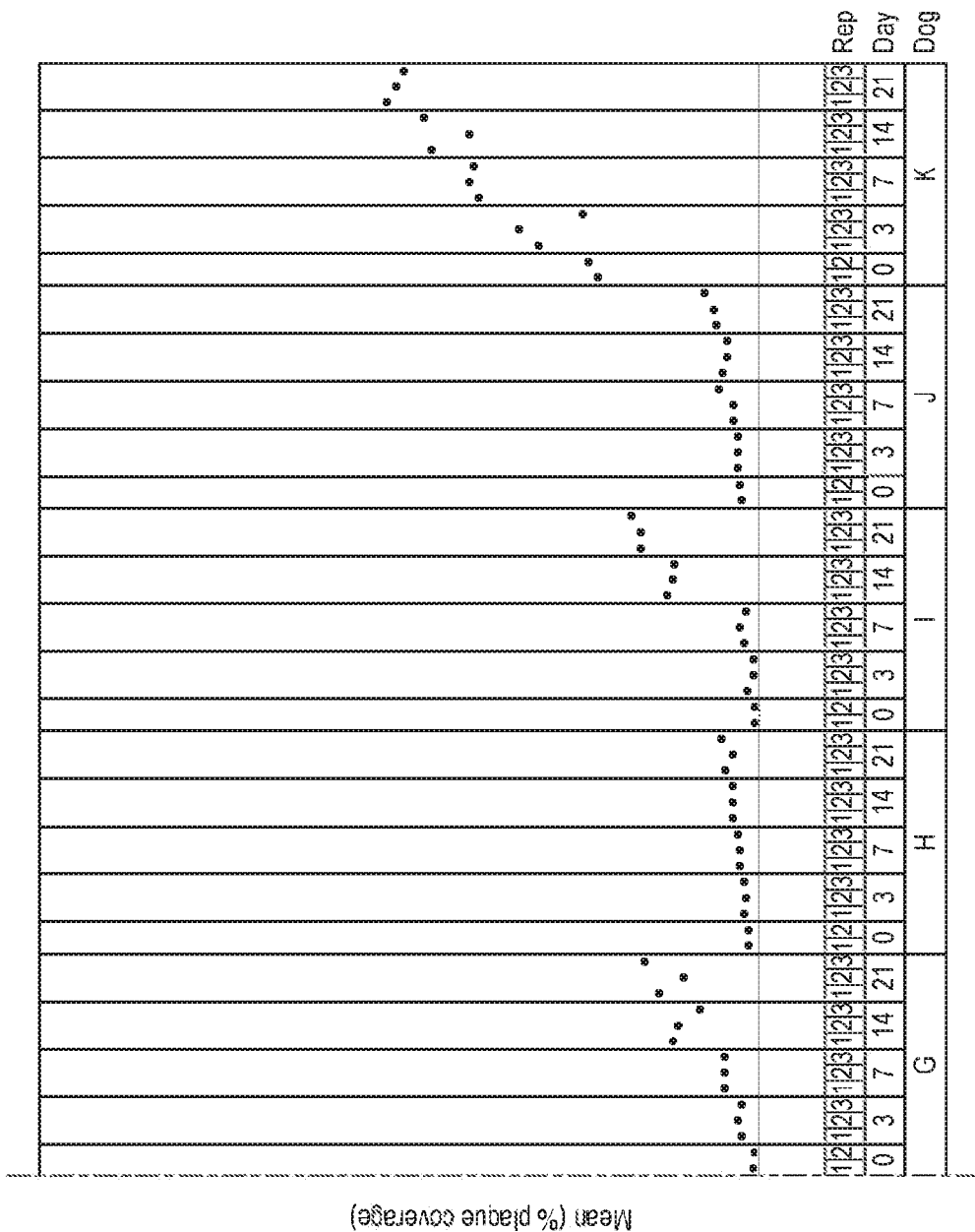

FIG. 8. Variability plot of percentage plaque coverage (whole mouth average: maxillary P1, P2, P3, P4), as determined by QLF™ on undisclosed teeth by dog (A-K), day (0, 3, 7, 14, 21) and repetition (1-3).

The percentage of plaque coverage can be measured on each of the maxillary premolars 3, 7, 14 and 21 days after stopping tooth brushing in conscious dogs.

Example 3: Longitudinal Assessment of Plaque Accumulation—Determining the Timeframes Over which Plaque Coverage can be Measured The aim of this example was to determine whether the levels of plaque coverage could be measured over time and at what stage it is possible to see a significant difference between treatment effects.

The trial demonstrates that product efficacy can be measured in conscious dogs over shorter time frames than the normal 28 day test phase.

This trial was designed to assess whether QLF™ could measure a product difference in conscious dogs at weeks 1, 2, 3 and 4 during the product test phase. 10 dogs were imaged consciously once a week for the duration of each 28 day test phase in the two phase cross over study. Only images of the maxillary I3, C, P3 and P4 were captured due to difficulties accessing the mandibular teeth in conscious dogs.

Statistics

The percentage plaque coverage, as measured by QLF™, was analyzed using a linear mixed effect model, with weighting by week specific variability to allow for increasing variance over time. Dog was included as a random effect to account for repeated measures on a dog and chew type, week and their interactions were included as fixed effects. Contrasts were performed between chew types at each week using a family wise controlled error rate of 5%. (R v3.02 using libraries nlme and multcomp).

Results

A significant difference was found between chew and no chew at weeks 1, 2, 3, and 4 (see FIG. 9. and Table 3) in whole mouth average plaque coverage (VOHC teeth I3, C, P3, P4).

After one week, a reduction in plaque coverage of 74% was observed (95% upper and lower confidence intervals of 54.3% and 93.6% respectively) when comparing chew to no chew (see Table 3).

TABLE 3

Percentage plaque reduction and significance when dogs received an oral care chew compared to no chew.

| Week | Mean % reduction in plaque coverage | Lower 95% confidence interval | Upper 95% confidence interval | P value |
| --- | --- | --- | --- | --- |
| 1 | −74 | −93.6 | −54.3 | <0.001 |
| 2 | −75.3 | −102.9 | −47.8 | <0.001 |
| 3 | −64.2 | −104 | −24.5 | <0.001 |
| 4 | −66.4 | −107.6 | −25.2 | <0.001 |

Figure 9:
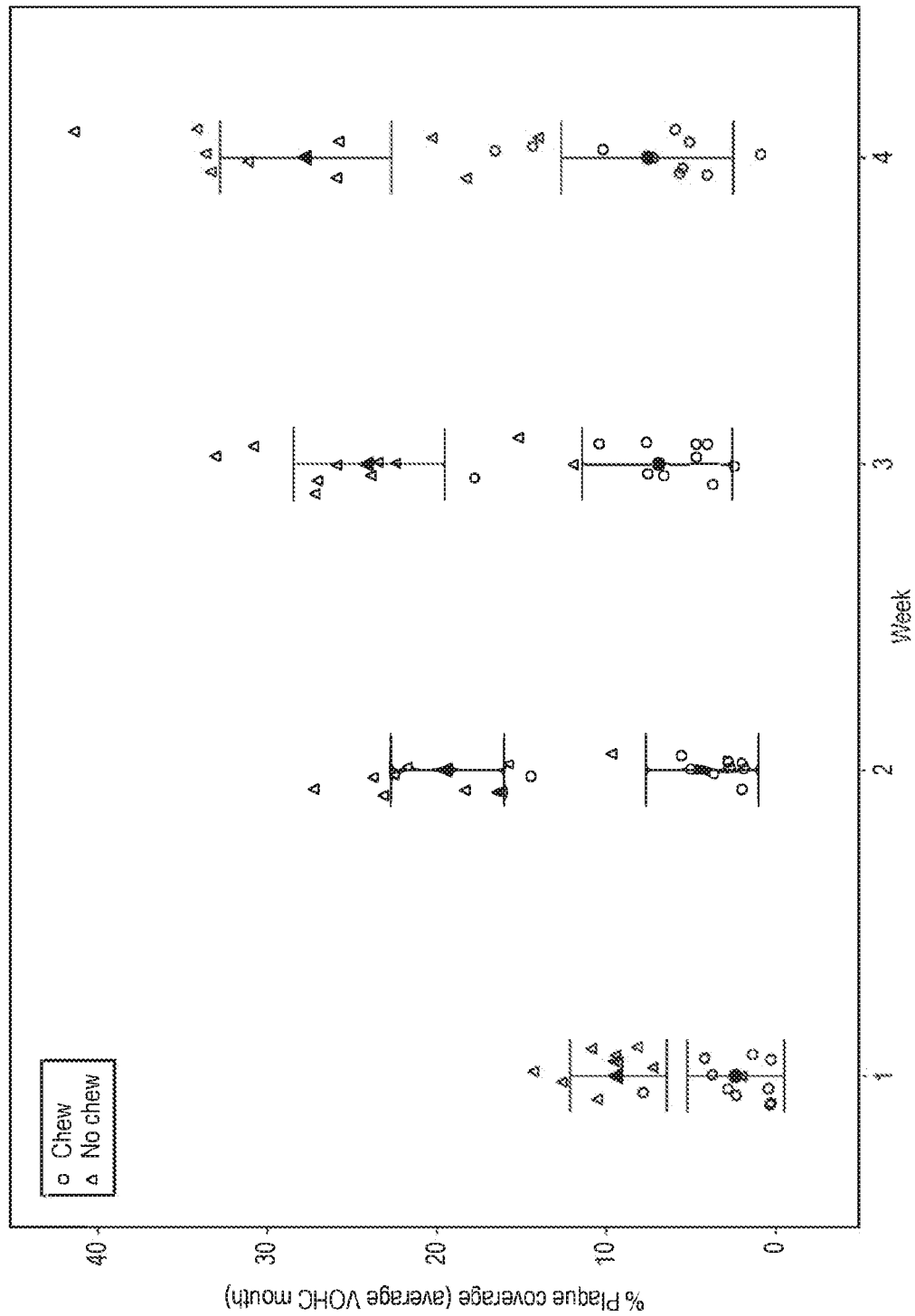
FIG. 9: Shows the whole mouth average percentage plaque (maxillary I3, C, P3 and P4) at 1, 2, 3 and 4 weeks in conscious dogs fed an oral care chew (circles) compared to no chew (triangles). Means are shown as solid shapes with 95% confidence intervals.

FIG. 9. Whole mouth average percentage plaque (maxillary I3, C, P3 and P4) at 1, 2, 3 and 4 weeks in dogs fed an oral care chew (circles) compared to no chew (triangles). Solid shapes illustrate the means and bars depict 95% confidence intervals.

In conclusion, this study showed that QLF™ images can be acquired of the maxillary teeth in conscious dogs and that a significant difference in the percentage reduction in plaque accumulation, between dogs fed an oral care chew and those receiving no chew, can be determined in time-frames as short as seven days.

Example 4: Assessing the Accuracy of the QLF™ Software

The ability of the QLF™ software to identify plaque correctly was determined by comparison with plaque coverage levels determined by five human scorers manually marking plaque on QLF™ acquired image.

Figure 10:
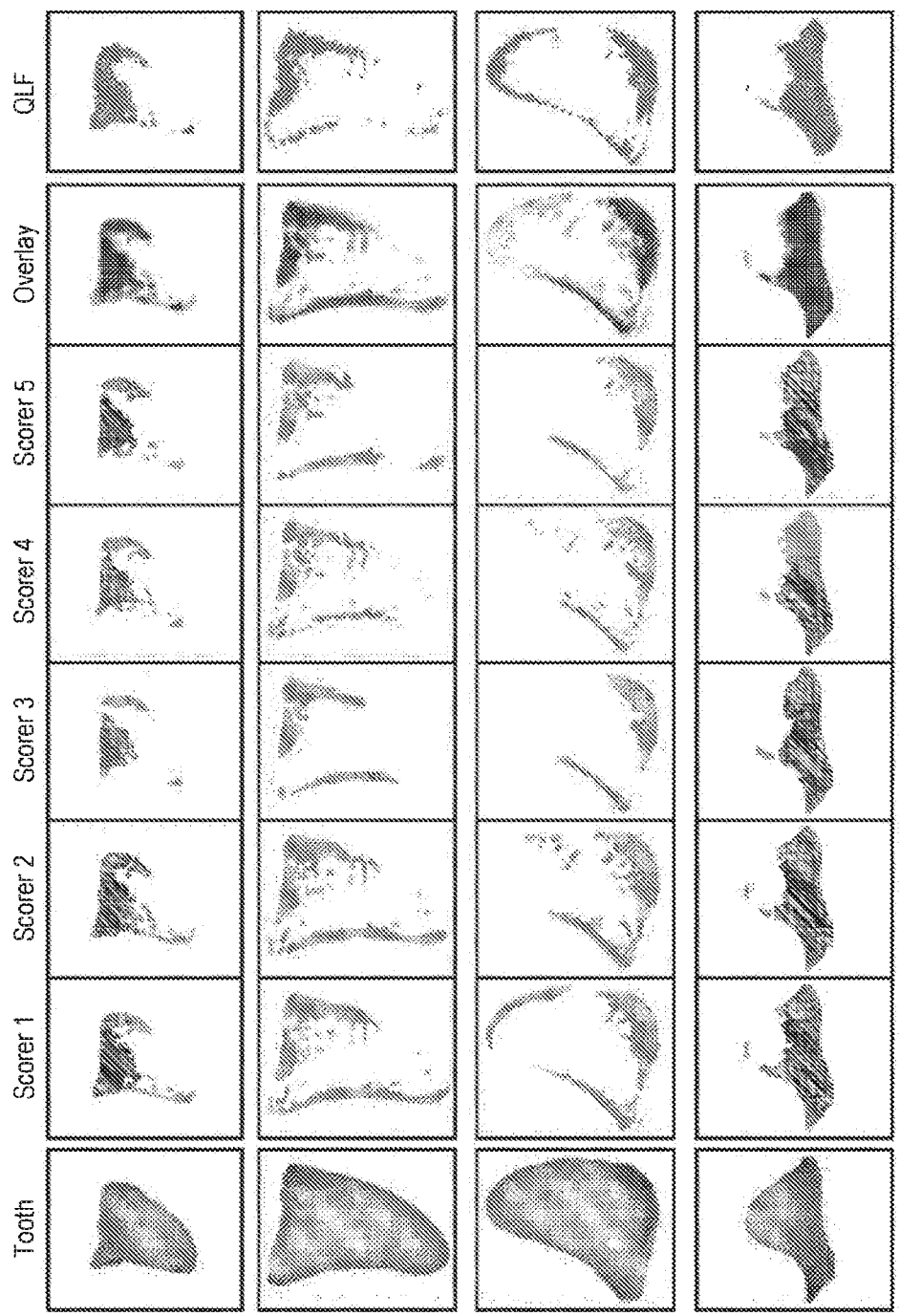
FIG. 10: Visual representation of the plaque identified by five human scorers marking plaque in Photoshop and plaque identified by QLF™ software, on four sample disclosed teeth.

QLF™ software results were compared to those from five trained human plaque scorers using photographs of 50 teeth with a range of plaque coverages. See FIG. 10. FIG. 10: Visual representation of the plaque identified by five human scorers marking plaque in Photoshop and plaque identified by QLF™ software, on four sample disclosed teeth.

Whole mouth scores from nine dogs, as assessed by five human scorers, were analyzed by a linear mixed model with scorer nested in dog fitted as the random effects. The variance estimates were then used to inform a simulation of 1000 scorers (with an average plaque coverage as found from the five human scorers). The probability of the QLF™ software results falling within the distribution of the human scorers' results was calculated by the percentage of simulated scorers with an average less than the average QLF™ software score. A test level of 5% was used.

Figure 11:
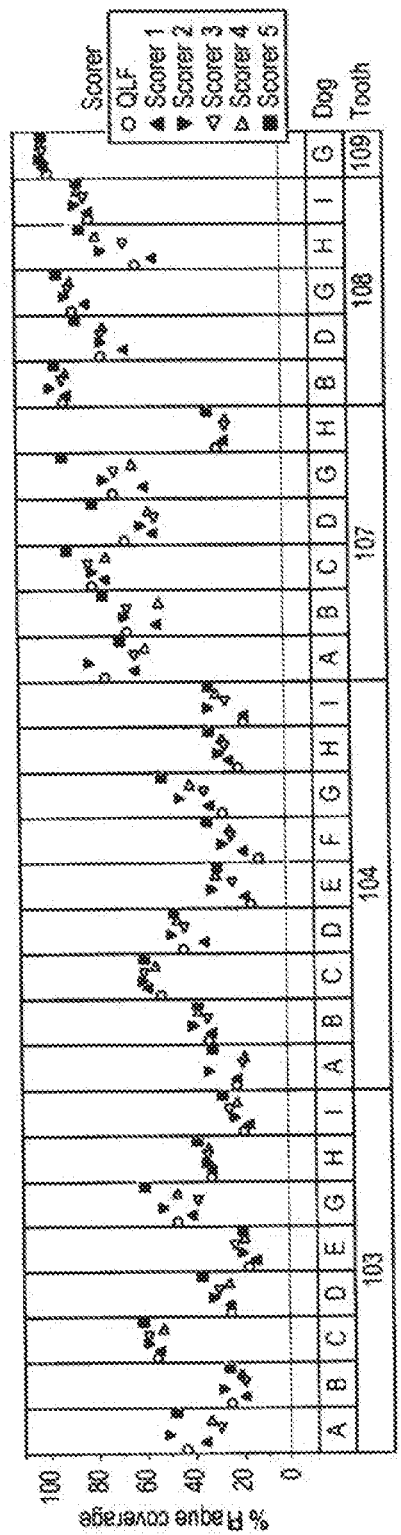
FIG. 11: Variability chart of average percentage plaque coverage identified by five human scorers marking plaque in Photoshop (triangles and squares) and QLF™ software (the circles) on maxillary $3^{rd}$ incisors, maxillary and mandibular canines and $3^{rd}$ and $4^{th}$ premolars (disclosed teeth) [103, 104, 107, 108 and 109 and 404, 407, 408 and 409].
Figure 11:
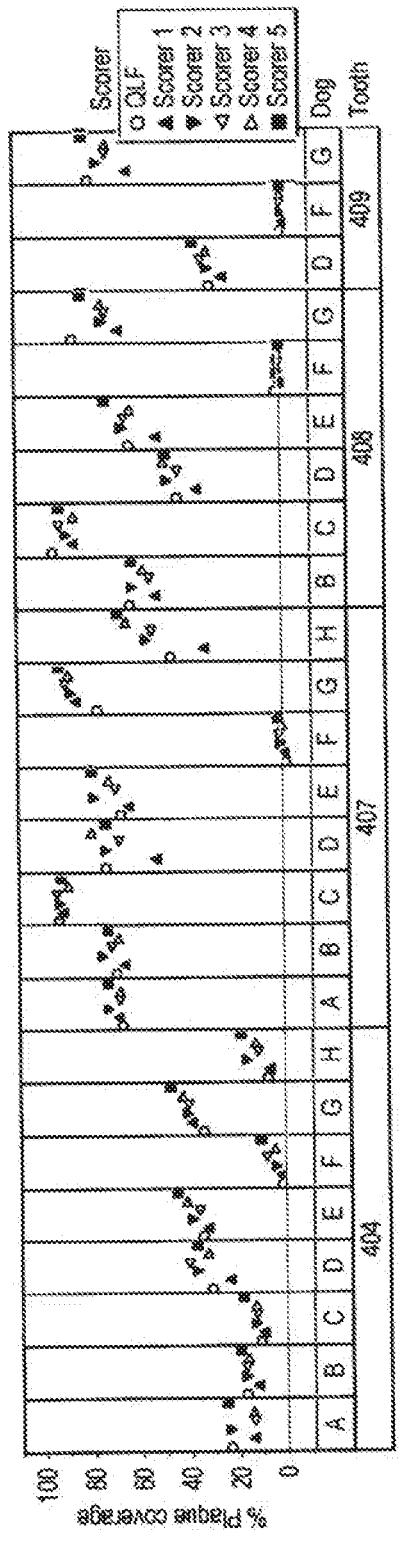

There was a high level of agreement in identification of plaque seen between the five scorers and QLF™ software across the entire range of plaque coverage from 0.6% to 100% (min, max). Simulations of the variance of the five scorers showed the QLF™ software was not significantly different to the human scorers with 10% of simulated human scorers having lower average percentage plaque coverage than the QLF™ software (p=0.1). See FIG. 11. FIG. 11: Variability chart of percentage plaque coverage identified by five human scorers marking plaque in Photoshop (the triangles and squares) and QLF™ software (the circles) on maxillary 3rd incisors, maxillary and mandibular canines and $3^{rd}$ and $4^{th}$ premolars (disclosed teeth). FIG. 11a shows the results from the teeth analyzed in the upper jaw (103, 104, 107, 108 and 109) and FIG. 11b shows the results from the teeth analyzed in the lower jaw (404, 407, 408, 409). The teeth analyzed are the mandibular and maxillary VOHC teeth used in standard clinical scoring studies.

Example 5: Comparison of QLF™ to Modified Logan and Boyce

This study compared QLF™ to the established plaque scoring method modified Logan and Boyce (Hennet et al., 2006).

Modified Logan & Boyce uses disclosed plaque and dissects tooth into gingival and coronal halves, and a score is then assigned between 0 and 4 dependant on the percentage plaque coverage on that half and a score between 1 and 3 dependent on the thickness of the plaque. The overall plaque score for each tooth half (gingival and coronal) was calculated by multiplying the coverage and thickness scores. Gingival and coronal scores were then added to give the total tooth score. The mean of all tooth scores provided the mouth score. The following teeth were included in the assessments: Maxillary I3, C, P2, P3, P4 and $1^{st}$ molar (M1; 109, 209), and mandibular C, P2, P3, P4 and M1 (309,409).

Dogs were maintained on a commercial adult dry diet and a product efficacy study was conducted as previously described. The plaque on the dog's teeth was visualized by the use of a disclosing solution and the amount of plaque determined using modified Logan & Boyce (Hennet et al., 2006) and QLF™. Data were analyzed by linear mixed effects models, with dog as a random effect to account for repeated measures and product as a fixed effect. Products were compared at the 5% test level.

Good agreement between QLF™ and the modified Logan and Boyce method was demonstrated in the percentage reduction of plaque accumulation between dogs fed an oral care chew versus no chew (Table 4). The methods gave similar results with product efficacy measured as a 22% reduction in plaque build-up by modified Logan and Boyce and a 19% reduction as measured by QLF™ when comparing dogs fed an oral care chew versus no chew. The reduction in plaque accumulation as measured by QLF™ is within the 95% confidence intervals of the Logan and Boyce result, and the width of the confidence interval for the reduction seen with QLF™ is 52% of that with Logan and Boyce indicating less variability with QLF™.

TABLE 4

Comparison of product efficacy measured by QLF ™ and modified Logan and Boyce methods.

| Data set | Mean plaque measure (95% Confidence Interval) | | Percentage reduction | P value |
|---|---|---|---|---|
| | OC Chew | No chew | | |
| Modified Logan & Boyce index | 9.79 (8.83, 10.75) | 12.57 (11.54, 13.59) | 22.13 (12.64, 31.62) | <0.001 |
| QLF ™ disclosed percentage | 54.78 (51.72, 57.85) | 67.73 (64.48, 70.98) | 19.12 (14.09, 24.14) | <0.001 |

A retrospective power analysis showed fewer dogs would be required to measure a 15% reduction in plaque accumulation using QLF™ compared to using the modified Logan & Boyce methodology, with at least 90% power.

Figure 12:
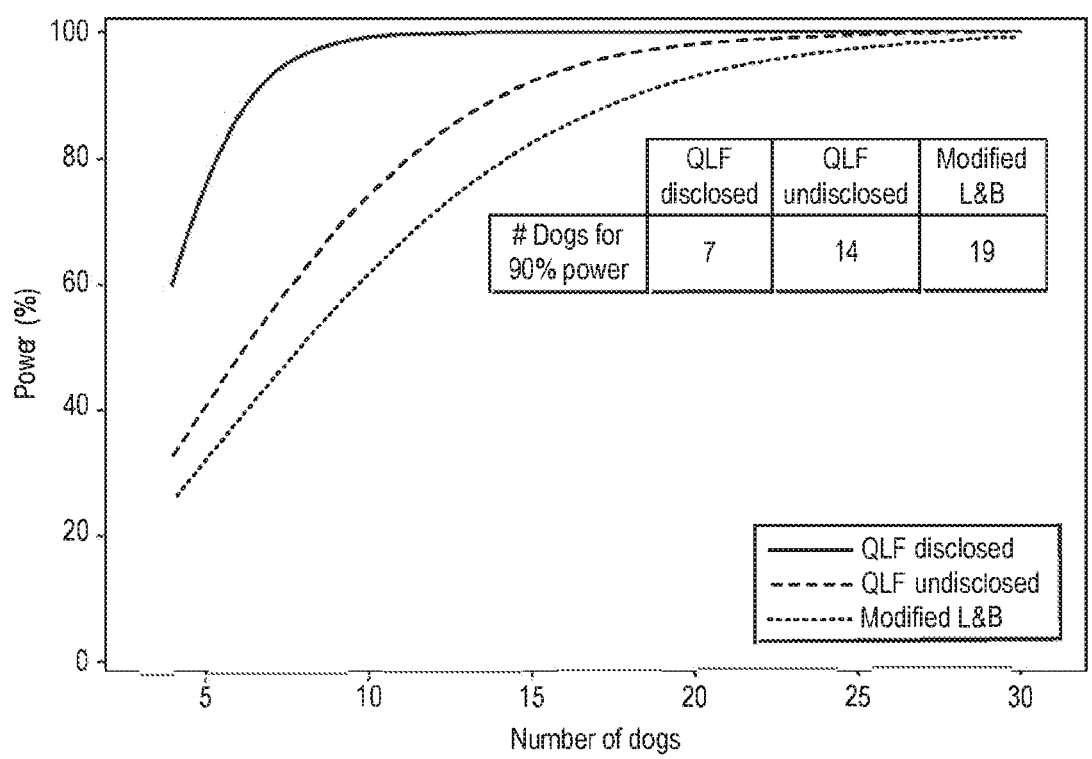
FIG. 12: Shows the power curves to detect a 15% reduction in plaque accumulation when fed an oral care chew compared to no chew in a two-way crossover trial (clean mouth model).

FIG. 12 shows the power curves to detect a 15% reduction in plaque accumulation when fed an oral care chew compared to no chew in a two-way crossover trial (26 dogs, clean mouth model). Solid line depicts QLF™ (disclosed teeth), dashed line modified Logan & Boyce and the dot dashed line QLF™ (undisclosed teeth). To measure a 15% reduction would require seven dogs with QLF™ compared to 19 with the Logan & Boyce methodology (90% power).

QLF™ is less subjective than modified Logan & Boyce. It is also faster; photographers require less training and the images can be stored to provide a permanent database for future use. In addition, fewer animals are required to measure the same size effect in dental product efficacy trials.

In summary, the percentage reduction in plaque accumulation as measured by QLF™ was in the range of that determined using modified Logan & Boyce. In addition, fewer animals are required to measure the same size effect in dental product efficacy trials. The use of fewer animals and the ability to undertake studies in conscious dogs supports two of the guiding principles underpinning the humane use of animals in scientific research; namely reducing the number of animals used to a minimum and refining the way experiments are carried out to improve animal welfare.

Example 6: Conscious Vs Non-Conscious Dogs

A method for measuring plaque in conscious dogs over a short time frame is highly desirable for testing new or improved oral care products (as opposed to the 28 day standard test trials).

Dogs were trained for conscious QLF™ imaging including:
With/without disclosing solution;
Plastic cheek retractors to view pre-molars;
Upper jaw only.

QLF™ images of undisclosed teeth were also taken of dogs consciously at the end of each test phase of the cross-over study prior to being placed under anaesthesia.

Figure 13:
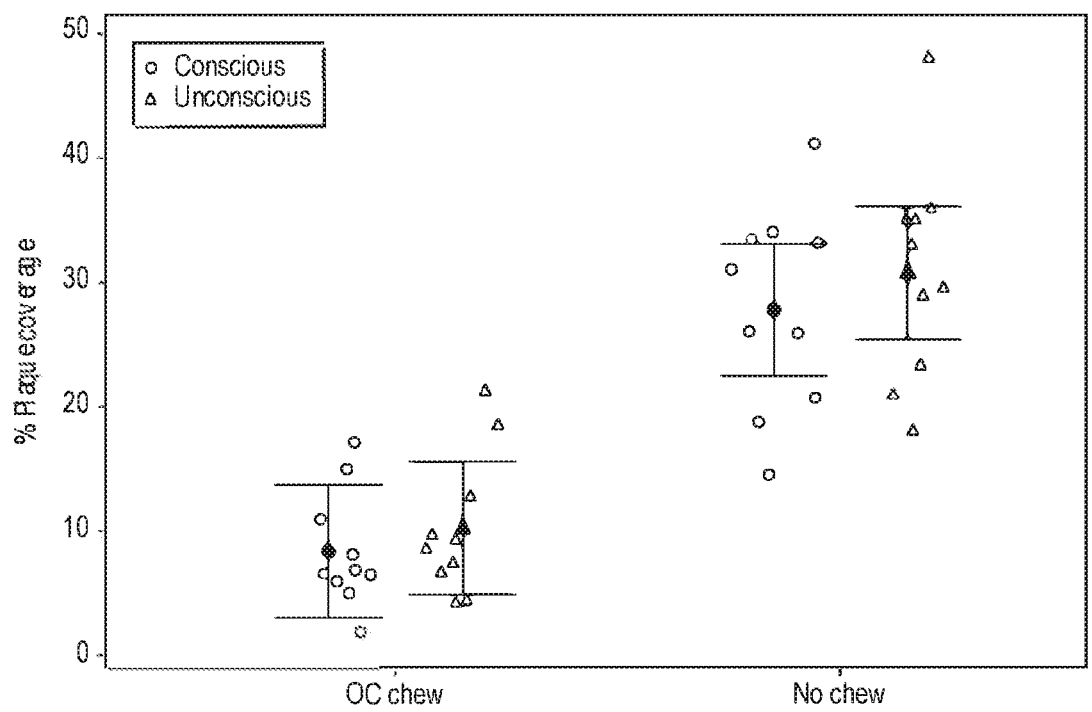
FIG. 13: Represents a chart of the average plaque coverage of maxillary jaw only (I3, C, P3, P4) of conscious dogs (circles) and maxillary (I3, C, P3, P4, M1) and mandibular (C, P3, P4, M1) jaw of unconscious dogs (triangles) when fed an oral care chew vs. no chew. Means are shown as solid shapes with 95% confidence intervals.

The percentage plaque coverage as measured by QLF™ of undisclosed teeth from conscious dogs (average of upper jaw teeth) and anaesthetised dogs (average of all VOHC teeth), was analyzed using linear mixed models, with dog as a random effect to account for repeated measures on a dog and measure type, product and their interactions as fixed effects. The contrast between chew types was compared between measures at the 5% level. This is shown in FIG. 13 which represents a chart of the average plaque coverage (y-axis) of maxillary jaw only (I3, C, P3, P4) of conscious dogs (circles) and maxillary (I3, C, P3, P4, M1) and mandibular (C, P3, P4, M1) jaw of unconscious dogs (triangles) when fed an oral care chew vs. no chew (x-axis). The bars depict 95% confidence intervals.

There was a significant difference between oral care chew and no chew for both dogs imaged consciously (P<0.001) and the same ten dogs imaged unconsciously (P<0.001)

The average plaque coverage for the dogs that were imaged consciously (undisclosed) was 27.7% (22.2%, 33.2%) and 7.6% (2.1%, 13.1%) for no chew and oral care chew respectively which is a 72.6% (54.0%, 91.2%) reduction in plaque accumulation. When the same ten dogs were imaged under anaesthesia (undisclosed) the average plaque coverage was 30.5% (25.0%, 36.1%) for no chew and 9.5% (4.0%, 15.0%) when fed an oral care chew which is a reduction in plaque accumulation of 69.0% (52.1%, 85.8%). This is shown in Table 5 below.

TABLE 5 showing the statistical results

| Data set | Oral care chew | No chew | % plaque reduction | P value |
|---|---|---|---|---|
| QLF ™ conscious (n = 10) | 7.6% (2.1%, 13.1%) | 27.7% (22.2%, 33.2%) | 72.6% (54.0%, 91.2%) | <0.001 |
| QLF ™ unconscious (n = 10) | 9.5% (4.0%, 15.0%) | 30.5% (25.0%, 36.1%) | 69.0% (52.1%, 85.8%) | <0.001 |

No significant difference was found between conscious and unconscious dogs in the percentage reduction in plaque accumulation between dogs fed the oral care chew and no chew (P=0.984).

In summary, product performance can be differentiated in conscious dogs as well as anesthetized dogs. In addition, there was no significant difference in the percentage reduction in plaque accumulation when dogs were fed an oral care chew compared to no chew when only the maxillary teeth (I3, C, P3, P4) were assessed as opposed to the whole mouth (VOHC teeth).

Example 7: Repeatability Study

The aim of the study was to evaluate the differences in the average plaque coverage over time between dogs receiving an oral care chew and no chew.

The study design was as described for example 1.

Undisclosed by Tooth Type:

A mixed model analyses was performed on the undisclosed data collected on days 0, 3, 7, 14 and 21. The random effects were fitted as day nested in tooth nested in dog. Tooth, day, chew and their interactions were fitted as fixed effects.

Figure 14A:
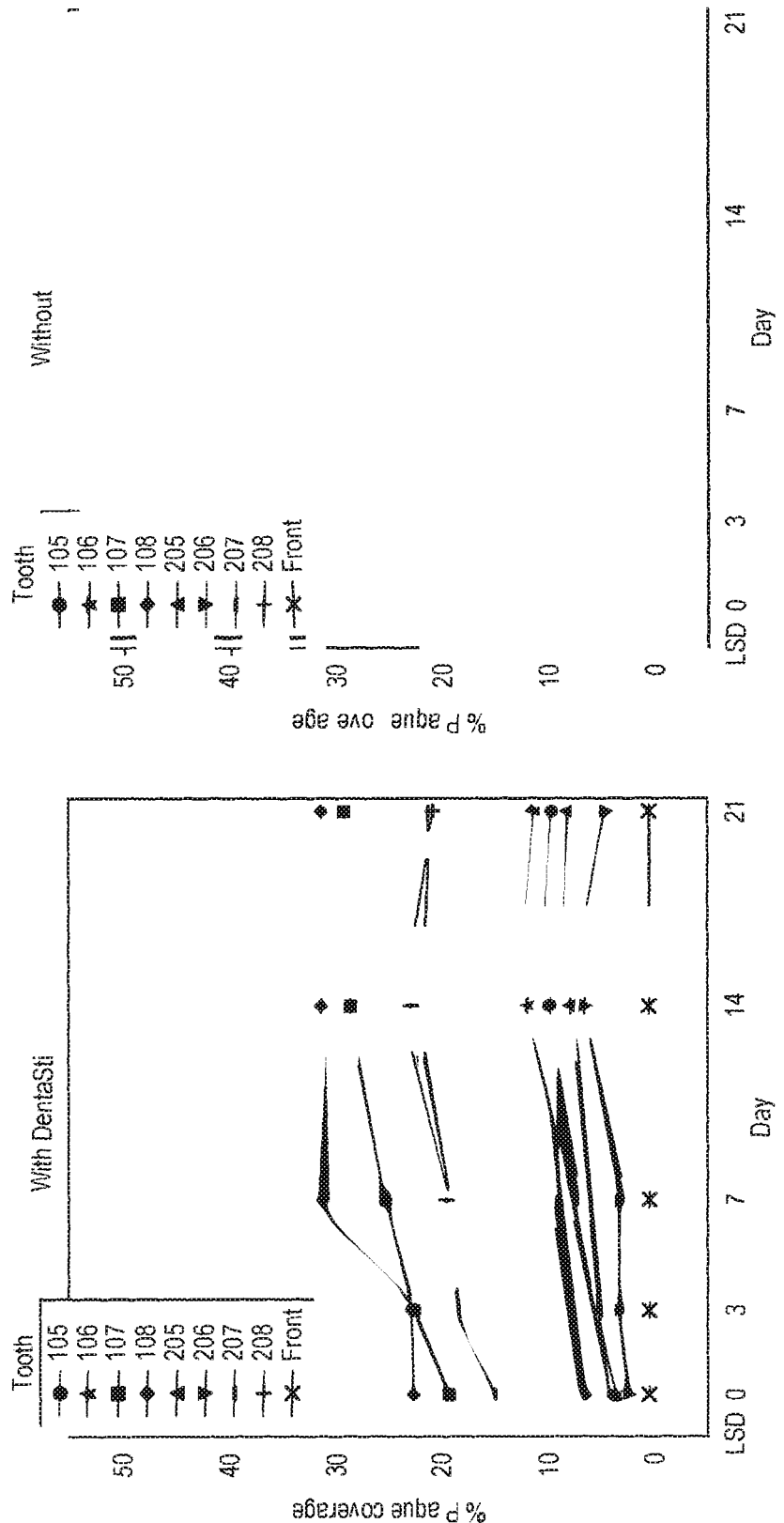
FIG. 14A: Shows mean % plaque coverage against day by tooth type with and without oral care chew respectively (LSD=least significant difference, bar represents the median difference between means needed for a significant difference at 5%), without baseline adjustment.

The interaction between tooth, day and chew is significant (p<0.001), thus the changes in coverage of plaque over the days changes with tooth type, and this was also different with the addition of an oral care chew (FIG. 14A).

There is a range in the average plaque coverage between tooth types on day 0 of the trial from 0% up to 23%, this range is slightly larger for the oral care chew dogs.

If multiplicity adjustments are made for the number of comparisons between tooth types at each time point (from day 0 for each time profile and between with and without oral care chew for each tooth type at each time point) then no significant changes with time are found with oral care chew presentation. There are significant increases from day 0 for teeth 107, 108, 207 and 208 without oral care chew presentation.

FIG. 14A: Mean % plaque coverage by day and tooth number with and without oral care chew respectively (LSD=least significant difference, bar represents the median difference between means needed for a significant difference at 5%).

To investigate the influence of day 0 variability on the results, the average repeat at day 0 was used as a covariate in a mixed model analyses, with day nested within tooth nested within dog as the random effects and chew, tooth, day and their interaction as fixed effects.

The interaction between tooth, day and chew is significant (p=0.002), thus the changes in coverage of plaque over the days changes with tooth type, and this is also different with the addition of an oral care chew.

Figure 14B:
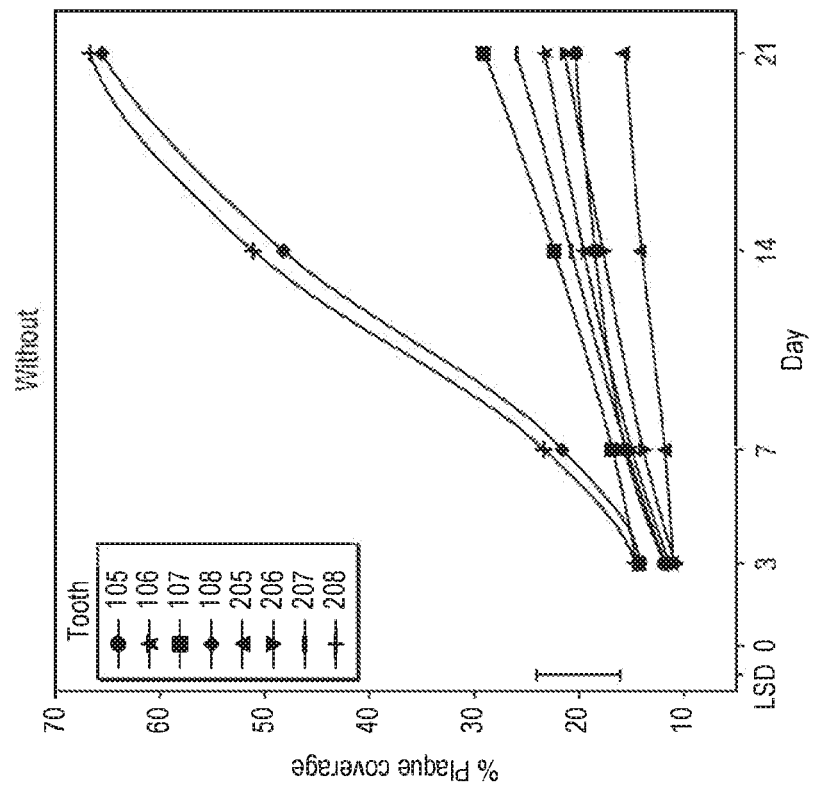
FIG. 14B: Shows mean % plaque coverage against day by tooth type with and without oral care chew respectively (LSD=least significant difference, bar represents the median difference between means needed for a significant difference at 5%), with baseline (day 0) adjustment.
Figure 14B:
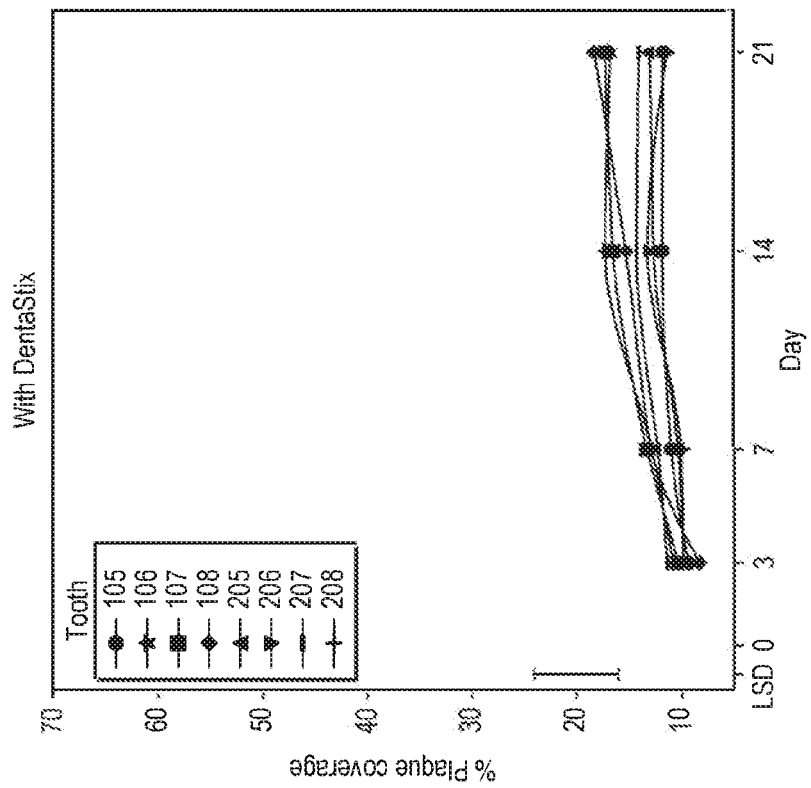

FIG. 14B: Mean percentage plaque coverage, adjusted for day 0, by day and tooth type, with and without oral care chew respectively (LSD=least significant difference, bar represents the median difference between means needed for a significant difference at 5%).

In conclusion, images of individual teeth of conscious dogs can be used to measure changes in quantities of plaque levels over time, even when not using a clean mouth model. Individual teeth can be used to differentiate between an oral care product compared to a control group.

Undisclosed Averaged Over Tooth Type (without Front), i.e. Average Mouth:

A mixed model analyses was performed on the undisclosed data collected on days 0, 3, 7, 14 and 21, excluding the front tooth data. The random effects were fitted as day nested in tooth nested in dog. Day, chew and their interaction were fitted as fixed effects.

Figure 15:
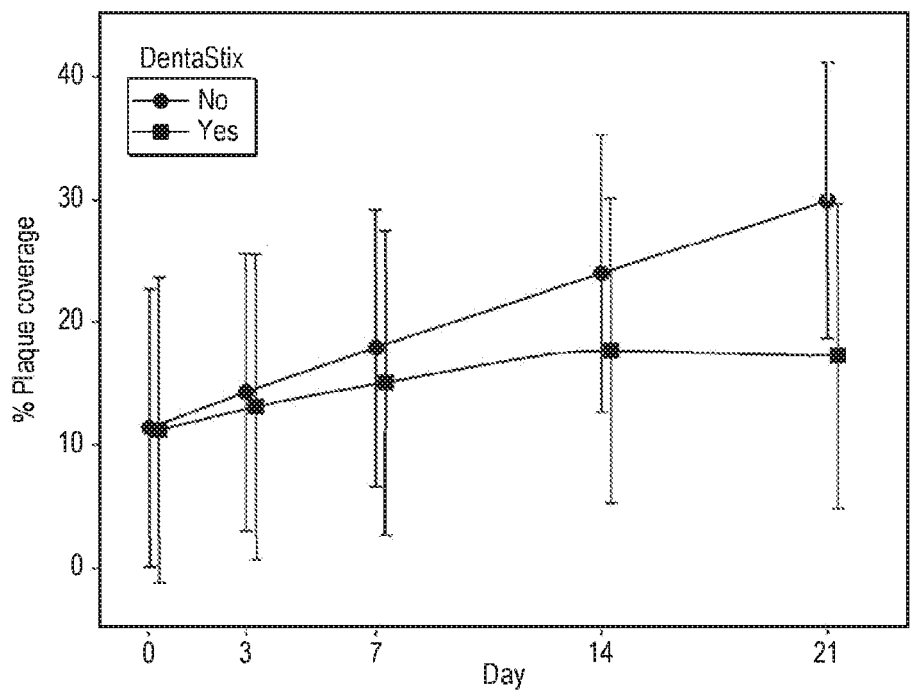
FIG. 15: Shows mean % plaque coverage against day by dogs fed daily oral care chew (squares) and those receiving no chew (circles), with 95% confidence intervals.

The interaction between day and chew is significant (p<0.001), thus the changes in coverage of plaque over the days is different if a chew is presented (see FIG. 15). FIG. 15 shows mean % plaque coverage against day by dogs fed daily oral care chew (square) and those receiving no chew (circle) with 95% confidence intervals.

Using a test level of 0.004 (=0.05/12–12–16 comparisons include the difference from day 0 to each time point within each chew, plus the comparison of the difference from day 0 to each time point between chews chew) it was found that:

Within chew, there were significant increases from day 0 at day 14 and day 21, p=0.001, where differences were larger than 6.0% (day 7 was significantly different at the unadjusted level, p=0.014);

Within no chew, there were significant increases from day 0 at day 7, 14 and 21, p<0.001, where differences ranges from 6.5% up to 18.4% (day 3 was significantly different at the unadjusted level, p=0.03);

Between chews, the difference from day 0 was higher at days 3, 7, 14 and 21 for no chew when compared to chew and significantly so at day 21, p<0.001 (day 14 was significantly different at the unadjusted level, p=0.005).

Thus the interaction is due to the quicker increase in average % plaque in the no chew group. The table below illustrates these results with adjusted 95% confidence intervals for the differences over time with chew and without chew.

TABLE 6

Comparisons in average % plaque coverage with 95% confidence intervals and p-values [yes = chew and no = no chew].

| Comparison (time, chew) | Difference | Lower 99.69% | Upper 99.69% | Probability |
|---|---|---|---|---|
| 0 Yes vs 3 Yes | −2.005 | −7.19 | 3.18 | 0.156 |
| 0 Yes vs 7 Yes | −3.84 | −8.87 | 1.19 | 0.014 |
| 0 Yes vs 14 Yes | −6.392 | −11.37 | −1.41 | 0.001 |
| 0 Yes vs 21 Yes | −5.957 | −10.94 | −0.97 | 0.001 |
| 0 No vs 3 No | −2.941 | −7.52 | 1.63 | 0.030 |
| 0 No vs 7 No | −6.499 | −11.02 | −1.98 | 0.000 |
| 0 No vs 14 No | −12.541 | −17.04 | −8.04 | 0.000 |
| 0 No vs 21 No | −18.444 | −22.95 | −13.94 | 0.000 |
| 0v3 Yes vs 0v3 No | −0.936 | −6.750 | 4.881 | 0.601 |
| 0v7 Yes vs 0v7 No | −2.658 | −8.350 | 3.035 | 0.151 |
| 0v14 Yes vs 0v 14 No | −6.150 | −11.800 | −0.499 | 0.005 |
| 0v21 Yes vs 0v21 No | −12.487 | −18.140 | −6.833 | <0.001 |

In conclusion, significant increases in the percentage of plaque accumulation can be measured from as early as three days. Differences in the rate of plaque accumulation can be detected in when dogs are fed an oral care chew compared to no chew.

Example 8: Conscious 7 Day Trial Usinq QLF™ Methodology

The aim of this study was to use Quantitative light induced fluorescence on conscious dogs to quantify plaque build-up over each 7 day phase of the trial.

Thirteen miniature schnauzer dogs using a clean mouth model, i.e. they received a single scale and polish at the start of the trial to set their teeth to baseline no plaque or calculus.

Dogs were fed no chew or oral care chew daily for seven days in a randomised cross over design, i.e. each dog received both "treatments".

QLF™ imaging of plaque was performed QLF™ image capture software was used to analyse the images.

QLF levels were conducted on conscious dogs with the addition of disclosing solution to visualise thinner immature plaque that doesn't fluoresce under blue light. Thus the method is a hybrid of QLF and planimetry. The addition of colour filters enables disclosed plaque to be automatically calculated.

QLF was performed at the beginning and end of each seven day phase to give a baseline plaque measure to work from. Tooth brushing was used to reset the teeth to baseline plaque at the start of each phase. No general anaesthetic was required between each phase as the short nature of the trial meant limited calculus formed so an unconscious scale and polish was not required.

The method enables the visualisation of 8 teeth on the upper jaw (103, 203, 104, 204, 107, 207, 108 and 208) as indicators of plaque development/removal.

Statistics

Image analysis of plaque levels was performed using analysis software. For each tooth the data takes the form of counts of fluoresced/stained pixels over total tooth area pixels to give percentage plaque coverage for each of the 8 indicator teeth (103, 203, 104, 204, 107, 207, 108 and 208) at each time point. The data set was analyzed in three ways:

% coverage of individual teeth. For each tooth, the % coverage at baseline was subtracted from the % coverage at the end of phase. This measure, % coverage corrected for baseline, was used as the response in a linear mixed model with treatment as the fixed effect and dog and tooth within dog as the random structure. Visual inspection of the residuals indicated no need for any transformation. A likelihood ratio test was used to assess the necessity of the tooth random effect and this resulted in the removal of this term.

Average % coverage across teeth. For each tooth, the % coverage at baseline was subtracted from the % coverage at the end of phase. For each dog, the average of these values was calculated. This measure, the average % coverage corrected for baseline, was used as the response in a linear mixed model with treatment as the fixed effect and dog as the random effect. Visual inspection of the residuals indicated no need for any transformation.

% coverage of the mouth. For each dog, the % coverage for the whole mouth was calculated at each measurement occasion by summing the fluoresced pixels across all teeth and dividing by the sum of the total pixels across all teeth, then multiplying by 100. The whole mouth % coverage at baseline was subtracted from the whole mouth % coverage at the end of phase. This measure, the whole mouth % coverage corrected for baseline, was used as the response in a linear mixed model with treatment as the fixed effect and dog as the random effect. Visual inspection of the residuals indicated no need for any transformation.

For all three models, estimates with 95% confidence intervals were extracted for each treatment and a between treatment comparison was performed.

Figure 16:
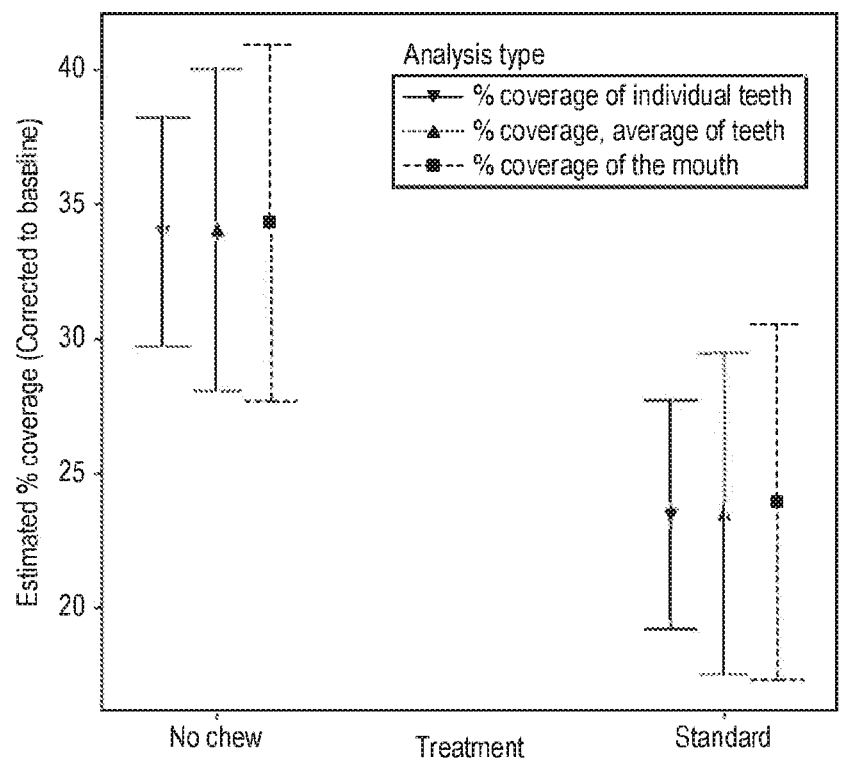
FIG. 16: Shows mean difference in % plaque coverage from baseline, with 95% confidence intervals, by dogs fed no chew and those fed a standard chew, using three different methods for quantifying mouth plaque coverage.

All three analyses showed a significant difference between the treatments (see FIG. 16).

16 shows all three results on the same graph. FIG. 16 shows all three results on the same graph with 95% confidence intervals for the mean. This demonstrates that it is possible to show significant differences in plaque coverage, in this case induced using a daily dental chew treatment, over a 7 day treatment phase. Differences were observed using all three different analysis methods showing that the data can be effectively interrogated at the level of single tooth differences through to whole mouth average plaque scores.

The first two methods give identical estimates as mathematically expected but the average across teeth appears more variable. The third method is the most variable and gives a slightly different estimate for the % coverage. This is expected since the first and second methods do not weight teeth by their size.

This study shows that plaque accumulation on individual teeth from a conscious companion animal can provide significant results and so significant differences can be determined in plaque removal when measuring specific indicator teeth. The use of conscious animals enables shorter study phases (as general anaesthesia's are not required between study phases the 4 week gaps recommended between general anaesthesia's are not required). Power analysis of this data shows that less animals are required to identify the same differences in plaque coverage than the current accepted gold standard measure of Modified Logan Boyce unconscious scoring.

In conclusion using QLF™ on conscious dogs allowed for shorter study treatment phases by removing the need for 4 week recovery times between general anesthesia. The study showed it was possible to show significant differences in plaque accumulation induced by oral care treatments using only indicator teeth on the upper jaw after a 7 day treatment phase.

Example 9: Validation of QLF™ on Unconscious Cats

The aim of this study was to quantify the variability and validate the use of QLF™ methodology to measure plaque in cats and the use of QLF™ on unconscious cats to demonstrate efficacy of a dental diet.

QLF images were taken of VOHC teeth (Upper=104, 204, 107, 207, 108, 208 and Lower=304, 404, 307, 407, 308, 408, 309, 409) in twenty four cats using a clean mouth model, ie they received a single scale and polish at the start of each study phase to set their teeth to a baseline of no plaque or calculus. The cats were fed either a standard Adult dry diet or a Dental dry diet daily for 28 days in a randomised cross over design, ie each cat received both "treatments". In addition to the QLF™ the Logan & Boyce (L&B) plaque scoring was also performed at the same time.

The study consisted of two phases, Phase 1—Repeatability and Phase 2—Reproducibility. For each phase the following measurements were taken (i) percentage plaque on each tooth assessed, (ii) average of the percentage of plaque on each tooth and (iii) weighted mouth–100*dividing the total plaque in mouth over total area in mouth.

A single assessor used QLF™ on cats under general anaesthesia with disclosing solution to quantify plaque accumulation at the end of each 28 day phase of the trial using hardware and image capture software. All 14 VOHC scoring teeth were imaged on upper and lower jaws as indicators of plaque development/removal. ie. 104, 204, 107, 207, 108, 208, 304, 404, 307, 407, 308, 408, 309 and 409. Images were analyzed using QLF™ analysis software.

At the end of a second phase of the efficacy study described above, disclosed plaque on the teeth of 12 cats was imaged by 3 photographers using QLF™ to determine reproducibility of results between different scorers. All 14 VOHC scoring teeth were imaged on upper and lower jaws as indicators of plaque development/removal. i.e., 104, 204, 107, 207, 108, 208, 304, 404, 307, 407, 308, 408, 309 and 409. Images were analyzed using QLF™ analysis software.

Statistics

Demonstrating Dental Diet Efficacy

The efficacy data were analyzed by linear mixed effect models (LMM). The average tooth, weighted mouth and L&B data used chew nested in cat as random effects and chew as a fixed effect. In addition, using the raw % plaque coverage data for each tooth, chew nested in tooth nested in cat were used as random effects and chew by tooth and their interaction as fixed effects. Means and differences between means were estimated with 95% family wise confidence intervals.

Repeatability and Reproducibility

To quantify the repeatability and reproducibility, variance components analyses were performed using LMM for each of the measures. Initially variance components were quantified for each VOHC tooth, by including repeat nested in cat as the random effects. The same model was used to analyze the average tooth and weighted mouth data. In addition, the % plaque on each tooth was analyzed (i.e. all data used rather than averaging prior to analyses) by including repeat nested in tooth nested in cat as the random effects. Variance components were extracted and the percentage of the total variance attributable to repeatability/reproducibility was quantified, along with the % coefficient of variation, relative to the overall mean of the respective data.

Results

Figure 17:
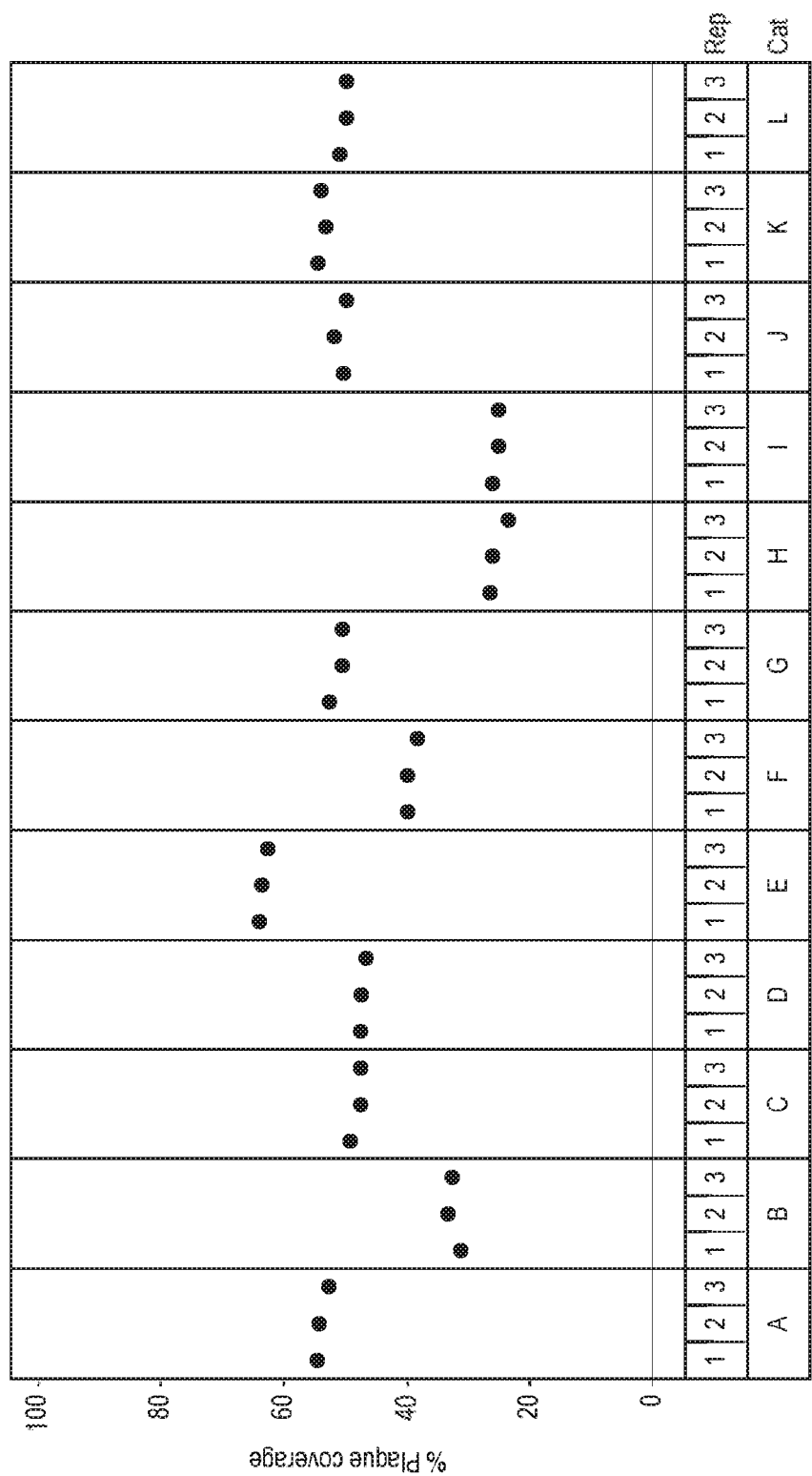
FIG. 17: (cat repeatability data) shows the average tooth percentage plaque coverage by cat for each repeat photograph.

The repeatability of the average tooth % plaque coverage by cat for each repeat photograph is shown in FIG. 17. The mean repeatability % CV was 2.2%.

Figure 18:
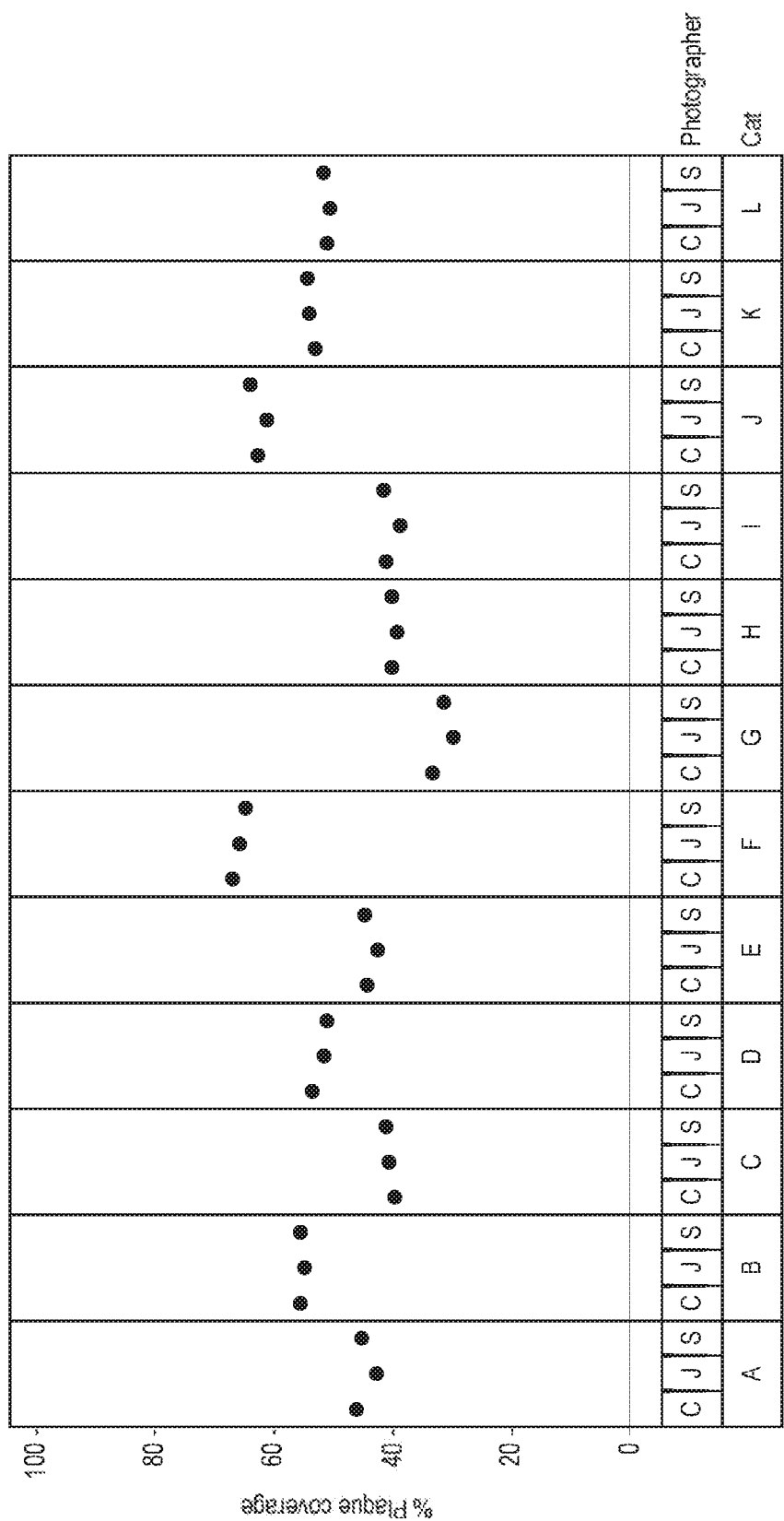
FIG. 18: (cat reproducibility data) shows the average tooth percentage plaque coverage by cat for each photographer.

The reproducibility of the average tooth % plaque coverage by cat for each of the three photographers is shown in FIG. 18. The mean reproducibility % CV was 2.3%.

Figure 19:
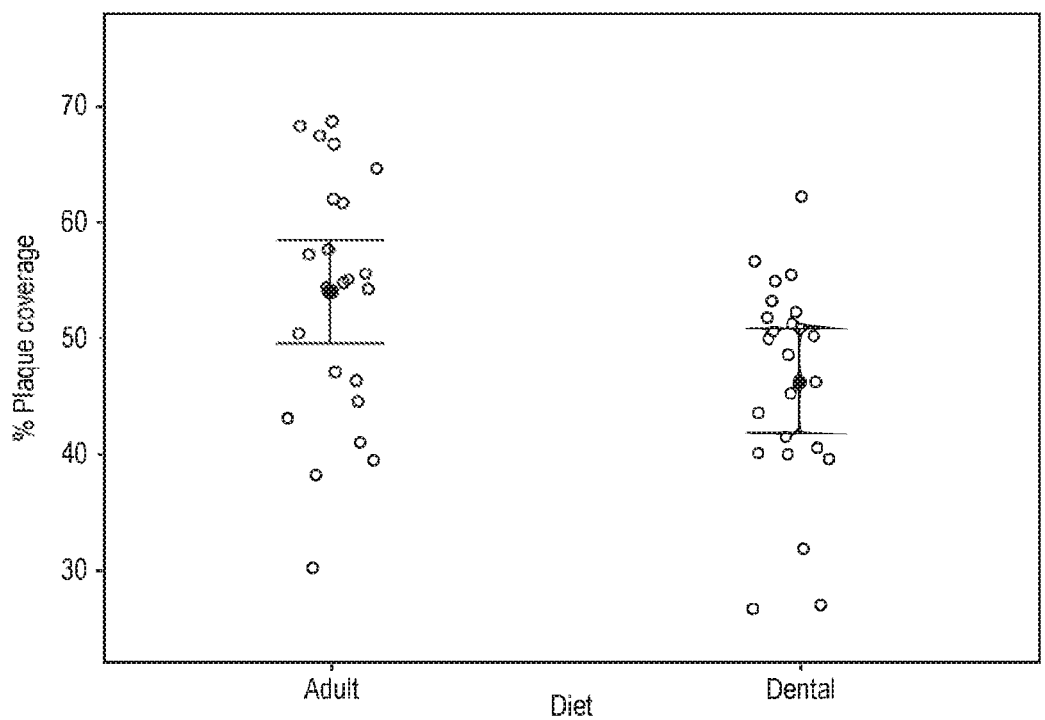
FIG. 19: (Cat dental diet efficacy) shows the mean average tooth percentage plaque coverage by diet and cat with 95% confidence intervals.

The dental diet efficacy results of the LMM analyses of the average tooth % plaque coverage showed a significant reduction in plaque coverage of approximately 14.26% (p<0.001) when fed the Dental diet, as shown in FIG. 19 with the 95% confidence intervals.

Figure 20:
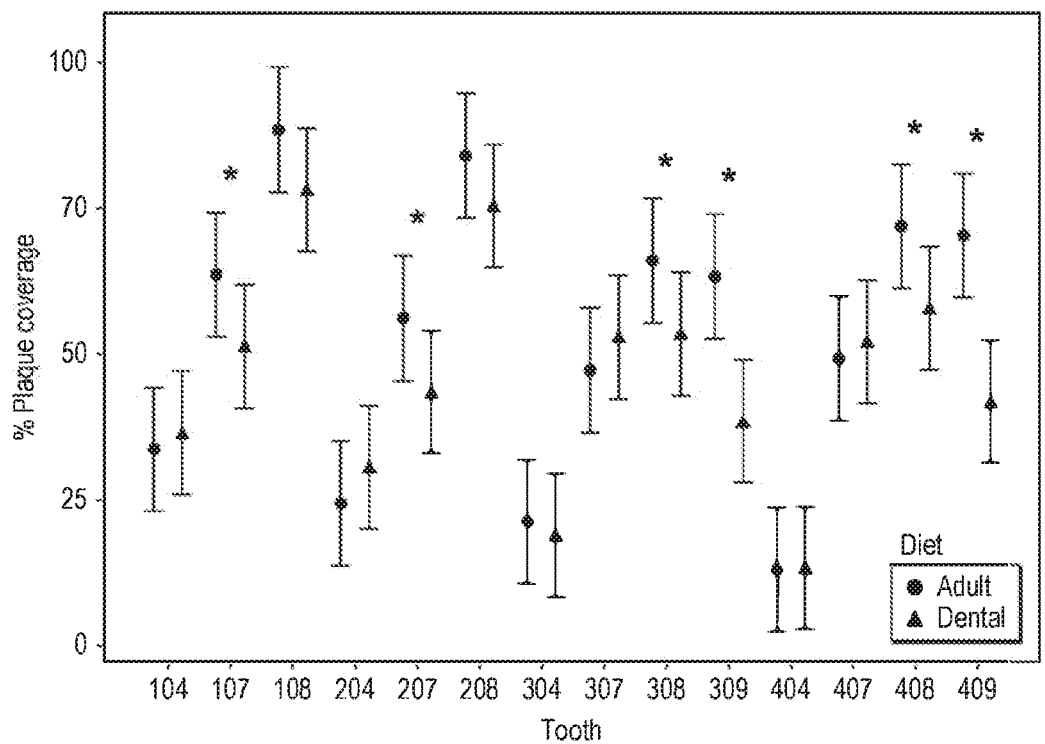
FIG. 20: shows the mean percentage plaque coverage for each tooth by diet, with 95% confidence intervals. Stars indicate significant differences between diets within tooth, p<0.05.

The LMM investigating the tooth by diet interaction showed the effect of diet to significantly change by tooth, p<0.0001. This interaction is illustrated in FIG. 20.

Further analyses were performed to investigate QLF in conscious cats, when photographing the following subsets of teeth:

104, 204, 107, 207, 108, 208, 304, 404, 307, 407, 308, 408, 309, 409
104 & 204 only
107 & 207 only
108 & 208 only
104, 204, 107, 207
107, 207, 108, 208
104, 204, 107, 207, 108, 208

The 7 subsets were then analyzed, by LMM with diet nested in tooth nested in cat as the random effects and diet as a fixed effect. FIG. 21 shows the subsequent results of Variance components and diet differences for various subsets of teeth. All subsets but the "104, 204, 107, 207" combination found a significant difference between diets. It can be seen that the use of only individual teeth 108/208 is sufficient.

In summary the trial demonstrated that using QLF™ it is possible to reproducibly quantify significant changes in plaque coverage in cats when fed specific dental diets, when using individual teeth (for example fewer than the VPOHC teeth, in particular the upper jaw teeth) as well as whole mouth assessments.

CONCLUSION

The data represents the validated reproducibility and accuracy of QLF™ and shows that QLF™ is a suitable technique for measuring plaque levels in dogs and in cats.

The data also shows that QLF™ can be used on conscious dogs and that the methodology provides significant differences to determine whole mouth assessments in animals by using data obtained on individual teeth (one or more teeth) in the mouth and one or more teeth in one jaw of the mouth (i.e. half mouth), in particular the upper jaw teeth as opposed to obtaining data in each and every tooth of the mouth to obtain the whole mouth assessment or as opposed to obtaining the entire list of recommended VOHC teeth.

The data provides evidence that trials can be conducted over fewer than 28 days.

The data provides evidence of a new rapid product testing methodology with increased accuracy allowing a shorter term for the trial and a lower number of animals tested. The data shows that trials can be conducted with shorter time frames for example, 7 days versus 28 day trials.

The data showed that trials measuring the efficacy of oral products in reducing plaque or tartar showed significant results at shorter time frames, showing evidence that trials can be conducted for at least 7 days as opposed to at least 28 days.

Further the examples of the invention show that accuracy of measuring the plaque and/or tartar in teeth can be achieved not only in shorter time frames (7 days versus 28 days) but also measuring half mouth vs full mouth. This was shown by only measuring the upper jaw of the subjects and then correlating the results to a full mouth percent plaque coverage measurement. The data shows significant results of trial lengths of 3, 7, 14 and 21 days, as well as significant results to conduct such trials using individual teeth (upper jaw) to correlate to full mouth measurements, as well as half mouth measurements correlated to full mouth measurements (i.e. upper jaw vs full mouth).

A particular advantage of the trials is the fact that the dogs were conscious. The results showed that there was no significant difference in the results between conscious and unconscious dogs.

The data shows that QLF™ is accurate, reproducible and a reliable method to be used on conscious dogs. It is capable of providing comparable results to the established clinical scoring methods, such as Logan & Boyce. Scoring requires much less training and is easily quantifiable using the software, thus less subjective. Fewer animals are required per trial and fewer teeth need to be analyzed, therefore providing trials which are shorter and faster to obtain results on product efficacy, and less stressful for the animal.

The invention claimed is:
1. A method of determining the efficacy of a test composition in reducing or preventing oral substrate in a companion animal, comprising:
   (i) obtaining one or more fluorescence images of one or more teeth of a conscious companion animal at the start of the trial (day 0); using Quantitative Light induced Fluorescent Technology (QLIFT)
   (ii) analysing the images to quantify the substrate coverage on the one or more teeth of the companion animal at the day 0;
   (iii) administering the companion animal with a test composition for the duration of the trial;
   (iv) obtaining one or more fluorescence images of the same one or more teeth of step (i) of the companion animal at pre-determined intervals during the trial using QLIFT;
   (v) analysing the images to determine and quantify the substrate coverage and size on each tooth of the companion animal and comparing the analysis of at least two images taken at the start of the trial or at each stage of the trial; and
   (vi) determining the efficacy of the test composition in reducing or preventing oral substrate in the companion animal;
   wherein the substrate coverage is qualitatively scored or quantified using image analysis software and wherein the companion animal has been trained to remain still for the duration of the obtaining the one or more images.

2. The method of claim 1, wherein the one or more teeth are located in the upper jaw of the companion animal.

3. The method of claim 2, wherein eight or fewer teeth are imaged.

4. The method of claim 1, wherein the substrate is selected from dental caries lesions, dental plaque, bacteria, calculus, staining, or any combination thereof.

5. The method of claim 1, wherein the companion animal is a dog or cat.

6. The method of claim 1, wherein the test composition is selected from a pet food stuff, pet treat, pet chew, or a combination of these.

7. The method of claim 1, wherein the trial period is from 3-7 days.

* * * * *